(12) United States Patent
Lopez

(10) Patent No.: US 7,717,886 B2
(45) Date of Patent: *May 18, 2010

(54) MEDICAL VALVE AND METHOD OF USE

(75) Inventor: George A. Lopez, Corona del Mar, CA (US)

(73) Assignee: ICU Medical, Inc., San Clemente, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 11/417,507

(22) Filed: May 3, 2006

(65) Prior Publication Data

US 2006/0264846 A1 Nov. 23, 2006

Related U.S. Application Data

(63) Continuation of application No. 10/630,131, filed on Jul. 30, 2003, now abandoned, which is a continuation of application No. 10/163,403, filed on Jun. 5, 2002, now Pat. No. 6,669,673, which is a continuation of application No. 09/569,712, filed on May 9, 2000, now Pat. No. 6,572,592, which is a continuation of application No. 08/905,370, filed on Aug. 4, 1997, now abandoned, which is a continuation of application No. 08/334,846, filed on Nov. 4, 1994, now Pat. No. 5,685,866, which is a continuation of application No. 08/096,659, filed on Jul. 23, 1993, now Pat. No. 5,695,466, which is a continuation-in-part of application No. PCT/US92/10367, filed on Dec. 1, 1992, now abandoned, which is a continuation-in-part of application No. 07/813,073, filed on Dec. 18, 1991, now abandoned.

(51) Int. Cl.
A61M 5/00 (2006.01)
(52) U.S. Cl. ..................................... 604/249

(58) Field of Classification Search ................. 604/246, 604/249
See application file for complete search history.

(56) References Cited

U.S. PATENT DOCUMENTS 1,578,517 A 3/1926 Hein
(Continued)

FOREIGN PATENT DOCUMENTS

CA 1105959 7/1981
(Continued)

OTHER PUBLICATIONS

PCT/SD/146, Jun. 14, 1994, Lopez.
(Continued)

*Primary Examiner*—Nicholas D Lucchesi
*Assistant Examiner*—Aarti B Berdichevsky
(74) *Attorney, Agent, or Firm*—Knobbe Martens Olson & Bear LLP

(57) ABSTRACT

A closed system, needleless valve device includes a generally tubular body defining an internal cavity. On the proximal end of the body there is an opening which is preferably sufficiently large to receive an ANSI standard tip of a medical implement. The distal end of the body has a generally tubular skirt. The valve also includes a hollow spike having a closed tip. The spike includes at least one longitudinal 18-gauge hole located distal the tip, and is seated inside the cavity such that the tip is below the proximal end of the body. An annular support cuff is connected to the spike which seals off a portion of the cavity of the body such that an upper cavity containing the tip is defined. The valve also includes a plastic, resilient silicone seal which fills the upper cavity and opening and covers the tip of the spike so as to present a flush surface. An adaptor enables the valve to be attached to a resealable container.

33 Claims, 19 Drawing Sheets

U.S. PATENT DOCUMENTS

| | | |
|---|---|---|
| 2,210,098 A | 8/1940 | Ravenscroft |
| 2,230,098 A | 1/1941 | Wurzburger |
| 2,289,677 A | 7/1942 | Perelson |
| 2,342,215 A | 2/1944 | Perelson |
| 2,387,512 A | 10/1945 | Hilberg |
| 2,577,780 A | 12/1951 | Lockhart |
| 2,667,986 A | 2/1954 | Perelson |
| 2,696,212 A | 12/1954 | Dunmire |
| 2,847,995 A | 8/1958 | Adams |
| 2,935,067 A | 5/1960 | Bouet |
| 2,999,499 A | 9/1961 | Willet |
| 3,033,046 A | 5/1962 | Rodda |
| 3,134,380 A | 5/1964 | Armao |
| 3,135,261 A | 6/1964 | Carroll |
| 3,172,205 A | 3/1965 | Gammon |
| 3,193,154 A | 7/1965 | Bross |
| 3,334,860 A | 8/1967 | Bolton, Jr. |
| 3,354,881 A | 11/1967 | Bloch |
| 3,376,866 A | 4/1968 | Ogle |
| 3,385,301 A | 5/1968 | Harautuneian |
| 3,416,567 A | 12/1968 | Von Dardel et al. |
| 3,500,821 A | 3/1970 | Ogle |
| 3,502,097 A | 3/1970 | Muller |
| 3,534,771 A | 10/1970 | Eyerdam et al. |
| 3,583,391 A | 6/1971 | Coz et al. |
| 3,585,984 A | 6/1971 | Buchanan |
| 3,630,199 A | 12/1971 | Gangarosa et al. |
| 3,648,684 A | 3/1972 | Barnwell et al. |
| 3,659,602 A | 5/1972 | Cloyd |
| 3,717,174 A | 2/1973 | Dewall |
| 3,734,080 A | 5/1973 | Petterson et al. |
| 3,788,519 A | 1/1974 | Mengal |
| 3,797,486 A | 3/1974 | Shaps |
| 3,806,086 A | 4/1974 | Cloyd |
| 3,813,791 A | 6/1974 | Stewart et al. |
| 3,830,241 A | 8/1974 | Dye et al. |
| 3,831,629 A | 8/1974 | Mackal et al. |
| 3,852,385 A | 12/1974 | Huggins |
| 3,861,388 A | 1/1975 | Vaughn |
| 3,882,863 A | 5/1975 | Sarnoff et al. |
| 3,886,930 A | 6/1975 | Ryan |
| 3,932,065 A | 1/1976 | Ginsberg et al. |
| 3,974,832 A | 8/1976 | Kruck |
| 3,976,063 A | 8/1976 | Henneman et al. |
| 3,976,073 A | 8/1976 | Quick et al. |
| 3,985,133 A | 10/1976 | Jenkins et al. |
| 3,986,508 A | 10/1976 | Barrington |
| 3,993,063 A | 11/1976 | Larrabee |
| 3,994,293 A | 11/1976 | Ferro |
| 4,005,710 A | 2/1977 | Zeddies et al. |
| 4,019,512 A | 4/1977 | Tenczar |
| 4,022,205 A | 5/1977 | Tenczar |
| 4,040,420 A | 8/1977 | Speer |
| 4,056,116 A | 11/1977 | Carter et al. |
| 4,059,109 A | 11/1977 | Tischlinger |
| 4,059,112 A | 11/1977 | Tischlinger |
| 4,066,067 A | 1/1978 | Micheli |
| 4,076,285 A | 2/1978 | Martinez |
| 4,079,737 A | 3/1978 | Miller |
| 4,079,738 A | 3/1978 | Dunn et al. |
| 4,080,965 A | 3/1978 | Phillips |
| 4,116,196 A | 9/1978 | Kaplan et al. |
| 4,121,585 A | 10/1978 | Becker, Jr. |
| 4,128,098 A | 12/1978 | Bloom et al. |
| 4,133,312 A | 1/1979 | Burd |
| 4,133,314 A | 1/1979 | Bloom et al. |
| 4,149,535 A | 4/1979 | Volder |
| 4,150,672 A | 4/1979 | Whitney et al. |
| 4,161,949 A | 7/1979 | Thanawalla |
| 4,185,628 A | 1/1980 | Kopfer |
| 4,187,846 A | 2/1980 | Lolachi et al. |
| 4,191,183 A | 3/1980 | Mendelson |
| 4,191,225 A | 3/1980 | Ogle |
| 4,201,208 A | 5/1980 | Cambio, Jr. |
| 4,204,538 A | 5/1980 | Cannon |
| 4,214,779 A | 7/1980 | Losell |
| 4,219,912 A | 9/1980 | Adams |
| 4,232,669 A | 11/1980 | Nitshke |
| 4,243,034 A | 1/1981 | Brandt |
| 4,243,150 A | 1/1981 | Gunne et al. |
| 4,256,106 A | 3/1981 | Shoor |
| 4,257,416 A | 3/1981 | Prager |
| 4,265,280 A | 5/1981 | Ammann et al. |
| 4,294,249 A | 10/1981 | Sheehan et al. |
| 4,296,949 A | 10/1981 | Muetterties et al. |
| 4,306,205 A | 12/1981 | Ito et al. |
| 4,306,705 A | 12/1981 | Svensson |
| 4,311,382 A | 1/1982 | Buckley et al. |
| 4,327,726 A | 5/1982 | Kwong et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,340,097 A | 7/1982 | Ammann et al. |
| 4,340,148 A | 7/1982 | Beckham |
| 4,343,550 A | 8/1982 | Buckley et al. |
| 4,362,156 A | 12/1982 | Feller, Jr. et al. |
| D269,545 S | 6/1983 | Cannon |
| 4,387,879 A | 6/1983 | Tauschinski |
| RE31,315 E | 7/1983 | Jenkins et al. |
| 4,392,499 A | 7/1983 | Towse |
| 4,392,851 A | 7/1983 | Elias |
| 4,405,163 A | 9/1983 | Voges et al. |
| 4,405,312 A | 9/1983 | Gross et al. |
| 4,411,662 A | 10/1983 | Pearson |
| 4,413,992 A | 11/1983 | Soika |
| 4,416,290 A | 11/1983 | Lutkowski |
| 4,417,890 A | 11/1983 | Dennehey et al. |
| 4,429,856 A | 2/1984 | Jackson |
| 4,432,759 A | 2/1984 | Gross et al. |
| 4,432,765 A | 2/1984 | Oscarsson |
| 4,439,188 A | 3/1984 | Dennehey et al. |
| 4,439,193 A | 3/1984 | Larkin |
| 4,440,207 A | 4/1984 | Genatempo et al. |
| 4,447,230 A | 5/1984 | Gula et al. |
| 4,449,539 A | 5/1984 | Sarstedt |
| 4,450,079 A | 5/1984 | Farr |
| D274,355 S | 6/1984 | Cannon |
| 4,452,473 A | 6/1984 | Ruschke |
| 4,457,749 A | 7/1984 | Bellotti et al. |
| 4,461,091 A | 7/1984 | Gammon |
| 4,464,179 A * | 8/1984 | Barger et al. ................ 604/250 |
| 4,470,664 A | 9/1984 | Shirasawa |
| 4,473,369 A | 9/1984 | Lueders et al. |
| 4,496,352 A | 1/1985 | Soika |
| 4,508,367 A | 4/1985 | Oreopoulos et al. |
| 4,511,359 A | 4/1985 | Vaillancourt |
| 4,512,766 A * | 4/1985 | Vailancourt ............ 604/167.03 |
| 4,515,591 A | 5/1985 | Hemmerich et al. |
| 4,535,820 A | 8/1985 | Raines |
| 4,537,216 A | 8/1985 | Schwartz et al. |
| 4,559,043 A | 12/1985 | Whitehouse et al. |
| 4,564,054 A | 1/1986 | Gustavsson |
| 4,573,974 A | 3/1986 | Ruschke |
| 4,583,917 A | 4/1986 | Shah |
| 4,589,879 A | 5/1986 | Pearson |
| 4,592,356 A | 6/1986 | Gutierrez |
| 4,601,703 A | 7/1986 | Herlitze |
| 4,607,868 A | 8/1986 | Harvey et al. |
| 4,610,469 A | 9/1986 | Wolff-Mooij |
| 4,614,437 A | 9/1986 | Buehler |
| 4,617,012 A | 10/1986 | Vaillancourt |
| 4,619,640 A | 10/1986 | Potolsky et al. |
| 4,623,068 A | 11/1986 | Brown et al. |

| | | | | | |
|---|---|---|---|---|---|
| 4,624,667 A | 11/1986 | Ktnarak | 4,969,883 A | 11/1990 | Gilbert et al. |
| 4,629,159 A | 12/1986 | Wellenstam | 4,970,794 A | 11/1990 | Buckley |
| 4,637,934 A | 1/1987 | White | 4,979,941 A | 12/1990 | Ogle, II |
| 4,639,019 A | 1/1987 | Mittleman | 4,981,469 A | 1/1991 | Whitehouse et al. |
| 4,645,494 A | 2/1987 | Lee et al. | 4,998,713 A | 3/1991 | Vaillancourt |
| 4,655,753 A | 4/1987 | Bellotti et al. | 4,998,921 A | 3/1991 | Vickory et al. |
| 4,666,429 A | 5/1987 | Stone | 4,998,927 A | 3/1991 | Vaillancourt |
| 4,673,400 A | 6/1987 | Martin | 5,006,114 A | 4/1991 | Rogers et al. |
| 4,676,228 A | 6/1987 | Krasner et al. | 5,009,490 A | 4/1991 | Kuono et al. |
| 4,679,571 A | 7/1987 | Frankel et al. | 5,018,532 A | 5/1991 | Ethridge, III |
| 4,683,916 A | 8/1987 | Raines | 5,020,562 A | 6/1991 | Richmond et al. |
| 4,698,207 A | 10/1987 | Bringham et al. | 5,024,616 A | 6/1991 | Ogle, II |
| 4,700,744 A | 10/1987 | Rutter et al. | 5,024,657 A | 6/1991 | Needham et al. |
| 4,706,487 A | 11/1987 | Bandou et al. | 5,033,476 A | 7/1991 | Kasai |
| 4,710,168 A | 12/1987 | Schwab et al. | 5,046,456 A | 9/1991 | Heyman et al. |
| 4,713,060 A | 12/1987 | Riuli | 5,047,021 A | 9/1991 | Utterberg |
| 4,725,267 A | 2/1988 | Vailancourt | 5,049,128 A | 9/1991 | Duquette |
| 4,730,635 A | 3/1988 | Linden | D321,250 S | 10/1991 | Jepson et al. |
| 4,735,607 A | 4/1988 | Keith, Jr. | D321,251 S | 10/1991 | Jepson et al. |
| 4,744,536 A | 5/1988 | Bancalari | D321,252 S | 10/1991 | Jepson et al. |
| 4,752,292 A | 6/1988 | Lopez et al. | 5,064,416 A | 11/1991 | Newgard |
| 4,759,756 A | 7/1988 | Forman et al. | 5,065,783 A | 11/1991 | Ogle, II |
| 4,767,412 A | 8/1988 | Hymanson | 5,066,287 A | 11/1991 | Ryan |
| 4,775,369 A | 10/1988 | Schwartz | 5,067,950 A | 11/1991 | Broadnax, Jr. |
| 4,778,453 A | 10/1988 | Lopez | 5,069,225 A | 12/1991 | Okamura |
| 4,781,702 A | 11/1988 | Herrli | 5,071,411 A | 12/1991 | Hillstead |
| 4,782,841 A | 11/1988 | Lopez | 5,085,645 A | 2/1992 | Purdy et al. |
| 4,784,650 A | 11/1988 | Coburn | 5,089,001 A | 2/1992 | Hwang |
| 4,790,829 A | 12/1988 | Bowden et al. | 5,098,405 A | 3/1992 | Peterson et al. |
| 4,790,832 A | 12/1988 | Lopez | 5,100,394 A | 3/1992 | Dudar et al. |
| 4,798,226 A | 1/1989 | Struth | 5,108,380 A | 4/1992 | Herlitze et al. |
| 4,798,605 A | 1/1989 | Steiner et al. | 5,113,911 A | 5/1992 | Hirsh |
| 4,804,366 A | 2/1989 | Zdeb et al. | D327,318 S | 6/1992 | Dudar et al. |
| 4,810,241 A | 3/1989 | Rogers | 5,122,123 A | 6/1992 | Vaillancourt |
| 4,813,938 A | 3/1989 | Raulerson | 5,134,489 A | 7/1992 | Sauer |
| 4,816,024 A | 3/1989 | Sitar et al. | 5,135,489 A | 8/1992 | Jepson et al. |
| 4,819,659 A | 4/1989 | Sitar | 5,147,333 A | 9/1992 | Raines |
| 4,819,684 A | 4/1989 | Zaugg et al. | 5,148,811 A | 9/1992 | Messinger |
| 4,823,833 A | 4/1989 | Hogan et al. | 5,154,703 A | 10/1992 | Bonaldo |
| 4,826,500 A | 5/1989 | Rautsola | 5,158,554 A | 10/1992 | Jepson et al. |
| 4,832,214 A | 5/1989 | Schrader et al. | 5,161,773 A | 11/1992 | Tower |
| 4,834,664 A | 5/1989 | Lin | 5,163,230 A | 11/1992 | Gast |
| 4,834,716 A | 5/1989 | Ogle, II | 5,163,922 A | 11/1992 | McElveen, Jr. et al. |
| 4,842,591 A | 6/1989 | Luther | 5,167,642 A | 12/1992 | Fowles |
| 4,846,805 A | 7/1989 | Sitar | 5,167,647 A | 12/1992 | Wijkamp et al. |
| 4,846,809 A | 7/1989 | Sims | 5,167,648 A | 12/1992 | Jepson et al. |
| 4,846,810 A | 7/1989 | Gerber | 5,171,231 A | 12/1992 | Heiliger |
| 4,850,978 A | 7/1989 | Dudar et al. | 5,171,234 A | 12/1992 | Jepson et al. |
| 4,852,620 A | 8/1989 | Jakubowicz et al. | 5,171,634 A | 12/1992 | Soszka et al. |
| 4,871,356 A | 10/1989 | Haindl et al. | 5,188,620 A | 2/1993 | Jepson et al. |
| 4,874,377 A | 10/1989 | Newgard et al. | 5,195,992 A | 3/1993 | Dudar et al. |
| 4,875,291 A | 10/1989 | Panique et al. | 5,195,994 A | 3/1993 | Dieringer |
| 4,875,760 A | 10/1989 | Youngren et al. | 5,199,947 A | 4/1993 | Lopez |
| 4,878,897 A | 11/1989 | Katzin | 5,201,725 A | 4/1993 | Kling |
| 4,880,414 A | 11/1989 | Whipple | 5,203,775 A | 4/1993 | Frank et al. |
| 4,889,527 A | 12/1989 | Herrli | 5,211,638 A | 5/1993 | Dudar et al. |
| 4,891,469 A | 1/1990 | Fick | 5,213,578 A | 5/1993 | Heiliger et al. |
| 4,895,562 A | 1/1990 | Lopez | 5,215,537 A | 6/1993 | Lynn et al. |
| 4,898,452 A | 2/1990 | Kawachi et al. | 5,242,393 A | 9/1993 | Brimhall et al. |
| 4,900,310 A | 2/1990 | Ogle, II | 5,242,413 A | 9/1993 | Heiliger |
| 4,907,879 A | 3/1990 | Webb | 5,242,425 A | 9/1993 | White et al. |
| 4,915,687 A | 4/1990 | Sivert | 5,242,432 A | 9/1993 | DeFrank |
| 4,917,668 A | 4/1990 | Haindl | 5,251,873 A | 10/1993 | Atkinson et al. |
| 4,919,167 A | 4/1990 | Manska | 5,255,441 A | 10/1993 | Burgess et al. |
| 4,928,212 A | 5/1990 | Benavides | 5,256,155 A | 10/1993 | Yerlikaya et al. |
| 4,931,048 A | 6/1990 | Lopez | 5,269,771 A | 12/1993 | Thomas et al. |
| 4,932,944 A | 6/1990 | Jagger et al. | 5,273,533 A | 12/1993 | Bonaldo |
| 4,934,655 A | 6/1990 | Blenkush et al. | 5,281,206 A | 1/1994 | Lopez |
| 4,943,896 A | 7/1990 | Johnson | 5,290,222 A | 3/1994 | Feng et al. |
| 4,946,445 A | 8/1990 | Lynn | 5,290,254 A | 3/1994 | Vaillancourt |
| 4,946,495 A | 8/1990 | Wada et al. | 5,295,657 A | 3/1994 | Atkinson |
| 4,950,260 A * | 8/1990 | Bonaldo ............... 604/535 | 5,297,776 A | 3/1994 | Dieringer |
| 4,964,855 A | 10/1990 | Todd et al. | 5,306,243 A | 4/1994 | Bonaldo |

| | | |
|---|---|---|
| 5,312,377 A | 5/1994 | Dalton |
| 5,322,518 A | 6/1994 | Schneider et al. |
| 5,323,539 A | 6/1994 | O'Neil |
| 5,324,270 A | 6/1994 | Kayan et al. |
| 5,330,450 A | 7/1994 | Lopez |
| 5,336,174 A | 8/1994 | Daoud et al. |
| 5,344,414 A | 9/1994 | Lopez et al. |
| 5,353,837 A | 10/1994 | Faust |
| 5,356,396 A | 10/1994 | Wyatt et al. |
| 5,360,413 A | 11/1994 | Leason et al. |
| 5,370,624 A | 12/1994 | Edwards et al. |
| 5,380,306 A | 1/1995 | Brinon |
| 5,385,547 A | 1/1995 | Wong et al. |
| 5,389,086 A | 2/1995 | Attermeier et al. |
| 5,401,245 A | 3/1995 | Haining |
| 5,411,499 A | 5/1995 | Dudar et al. |
| 5,423,753 A | 6/1995 | Fowles et al. |
| 5,439,451 A | 8/1995 | Collinson et al. |
| 5,449,145 A | 9/1995 | Wortrich |
| 5,470,319 A | 11/1995 | Mayer |
| 5,474,536 A * | 12/1995 | Bonaldo ............... 604/86 |
| 5,487,731 A | 1/1996 | Denton |
| 5,489,274 A * | 2/1996 | Chu et al. ............ 604/167.05 |
| 5,509,912 A | 4/1996 | Vaillancourt et al. |
| 5,520,666 A * | 5/1996 | Choudhury et al. ......... 604/537 |
| 5,549,566 A | 8/1996 | Elias et al. |
| 5,549,577 A | 8/1996 | Siegel et al. |
| 5,556,388 A | 9/1996 | Johlin, Jr. |
| 5,603,706 A | 2/1997 | Wyatt et al. |
| 5,676,346 A | 10/1997 | Leinsing |
| 5,685,866 A | 11/1997 | Lopez |
| 5,688,254 A | 11/1997 | Lopez et al. |
| 5,690,612 A | 11/1997 | Lopez et al. |
| 5,694,686 A | 12/1997 | Lopez |
| 5,695,466 A | 12/1997 | Lopez et al. |
| 5,700,248 A * | 12/1997 | Lopez ................ 604/249 |
| 5,730,418 A | 3/1998 | Feith et al. |
| 5,738,663 A | 4/1998 | Lopez |
| RE35,841 E | 7/1998 | Frank et al. |
| 5,776,116 A | 7/1998 | Lopez et al. |
| 5,776,125 A | 7/1998 | Dudar et al. |
| 5,785,692 A | 7/1998 | Attermeier et al. |
| 5,839,715 A * | 11/1998 | Leinsing ............... 251/149.1 |
| 5,873,862 A | 2/1999 | Lopez |
| 5,901,942 A | 5/1999 | Lopez |
| 5,928,204 A | 7/1999 | Lopez |
| 6,019,748 A | 2/2000 | Lopez |
| 6,113,068 A | 9/2000 | Ryan |
| 6,132,403 A | 10/2000 | Lopez |
| 6,132,404 A | 10/2000 | Lopez |
| 6,325,782 B1 | 12/2001 | Lopez |
| 6,428,520 B1 | 8/2002 | Lopez et al. |
| 6,572,592 B1 | 6/2003 | Lopez |
| 6,599,273 B1 | 7/2003 | Lopez |
| 6,635,044 B2 | 10/2003 | Lopez |
| 6,669,673 B2 * | 12/2003 | Lopez ................ 604/249 |
| 6,682,509 B2 | 1/2004 | Lopez |
| 6,695,817 B1 * | 2/2004 | Fangrow, Jr. ............ 604/167.01 |
| 6,758,833 B2 | 7/2004 | Lopez |
| 6,916,309 B2 | 7/2005 | Fangrow |
| 6,932,795 B2 | 8/2005 | Lopez et al. |
| 2002/0133124 A1* | 9/2002 | Leinsing et al. ............ 604/256 |
| 2003/0199835 A1* | 10/2003 | Leinsing et al. ............ 604/256 |
| 2004/0030321 A1* | 2/2004 | Fangrow, Jr. ............... 604/533 |
| 2004/0034325 A1 | 2/2004 | Lopez |
| 2004/0073174 A1 | 4/2004 | Lopez |
| 2004/0171993 A1* | 9/2004 | Bonaldo ............... 604/248 |
| 2004/0243070 A1 | 12/2004 | Lopez |
| 2006/0163515 A1* | 7/2006 | Ruschke ............... 251/149.7 |
| 2006/0200087 A1 | 9/2006 | Lopez |
| 2006/0200091 A1 | 9/2006 | Lopez |
| 2006/0200092 A1 | 9/2006 | Lopez |
| 2006/0206058 A1 | 9/2006 | Lopez |
| 2006/0206059 A1 | 9/2006 | Lopez |
| 2006/0264845 A1 | 11/2006 | Lopez |
| 2006/0264847 A1 | 11/2006 | Lopez |
| 2006/0264891 A1 | 11/2006 | Lopez |
| 2006/0264892 A1 | 11/2006 | Lopez |

FOREIGN PATENT DOCUMENTS

| | | |
|---|---|---|
| CA | 1305903 | 8/1992 |
| CA | 1308322 | 10/1992 |
| CA | 1315165 | 3/1993 |
| DE | 855 319 | 11/1952 |
| DE | 3303718 C1 | 10/1984 |
| EP | 0 240 590 | 4/1987 |
| EP | 0 309 771 | 3/1988 |
| EP | 0 319 764 | 6/1989 |
| EP | 0 399 119 | 7/1989 |
| EP | 0 446 463 | 12/1990 |
| EP | 0 446 469 A1 | 12/1990 |
| EP | 0 263 789 | 6/1991 |
| EP | 0472088 | 2/1992 |
| FR | 1373027 | 8/1964 |
| FR | 2439022 | 5/1985 |
| GB | 84 25 197 | 10/1985 |
| NO | 310805 | 6/1994 |
| WO | WO 86/01712 | 3/1986 |
| WO | WO 86/03415 | 6/1986 |
| WO | WO 86/03416 | 6/1986 |
| WO | WO 89/06553 | 7/1989 |
| WO | WO 90/12606 | 11/1990 |
| WO | WO 91/05581 | 5/1991 |
| WO | WO 91/06255 | 5/1991 |
| WO | WO 93/02724 | 2/1993 |
| WO | WO 94/01170 | 1/1994 |
| WO | WO 96/17646 | 6/1996 |

OTHER PUBLICATIONS

U.S. Appl. No. 08/265,095, filed Jun. 24, 1994, now abandoned.
U.S. Appl. No. 08/883,389, filed Jun. 26, 1997, now abandoned.
U.S. Appl. No. 08/486,851, filed Jun. 7, 1997, now abandoned.
U.S. Appl. No. 08/476,127, filed Jun. 7, 1995, now abandoned.
U.S. Appl. No. 08/475,595, filed Jun. 7, 1995, now abandoned.
U.S. Appl. No. 09/150,580, filed Sep. 10, 1998, now abandoned.
U.S. Appl. No. 10/630,131, filed Jul. 30, 2003, now abandoned.
U.S. Appl. No. 08/475,599, filed Jun. 7, 1995, now abandoned.
U.S. Appl. No. 08/479,681, filed Jun. 7, 1995, now abandoned.
U.S. Appl. No. 10/882,469, filed Jul. 1, 2004, pending.
U.S. Appl. No. 11/417,774, filed May 3, 2006, pending.
U.S. Appl. No. 11/418,531, filed May 3, 2006, pending.
U.S. Appl. No. 11/418,417, filed May 3, 2006, pending.
U.S. Appl. No. 10/607,946, filed Jun. 27, 2003, pending.
U.S. Appl. No. 11/417,642, filed May 3, 2006, pending.
U.S. Appl. No. 11/417,461, filed May 3, 2006, pending.
U.S. Appl. No. 11/417,452, filed May 3, 2006, pending.
U.S. Appl. No. 11/417,700, filed May 3, 2006, pending.
U.S. Appl. No. 11/381,527, filed May 3, 2006, pending.
U.S. Appl. No. 11/381,524, filed May 3, 2006, pending.
U.S. Appl. No. 11/381,526, filed May 3, 2006, pending.
U.S. Appl. No. 11/417,713, filed May 3, 2006, pending.
U.S. Appl. No. 11/417,669, filed May 3, 2006, pending.
U.S. District Court Civil Docket for *ICU Medical, Inc.* v. *Alaris Medical Systems, Inc.*, Filed in Case No. SA CV 04-0689, dated Jun. 24, 2008.
Findings of Fact Not Genuinely Contested and Conclusions of Law in support of the court's Jul. 17, 2006 order granting Alaris motion for partial summary of noninfringement of "Spike" claims signed by Mariana R. Pfaelzer, dated on Aug. 25, 2006, Filed in Case No. SA CV 04-0689.
Judgment granting defendant Alaris Medical Systems, Inc. motion for partial Summary Judgment of noninfringement of "Spike" Claims; Related to: findings of fact and conclusions of law 451 by Judge Mariana R. Pfaelzer, dated on Aug. 25, 2006, Filed in Case No. SA CV 04-0689.

Notice of Motion and Motion for Summary Judgment of invalidity of Spike-Less claims under 35 USC 112 filed by defendant Alaris Medical Systems, Inc., dated on Sep. 12, 2006, Filed in Case No. SA CV 04-0689.

Memorandum in Support of Motion for Summary Judgment of invalidity of Spike-Less claims under USC112 [484] filed by defendant Alaris Medical Systems, Inc., dated on Sep. 12, 2006, Filed in Case No. SA CV 04-0689

Declaration of Scott P. McBride in support of memorandum in support re Motion for Summary Judgment of invalidity of Spike-Less claims under 35 USC 112 [484] filed by defendant Alaris Medical Systems, Inc., dated on Sep. 12, 2006, Filed in Case No. SA CV 04-0689.

Notice of Motion and Motion for Summary Judgment of noninfringement of all remaining claims filed by defendant Alaris Medical Systems, Inc., dated on Sep. 29, 2006, Filed in Case No. SA CV 04-0689.

Declaration of David Headrick in support of Motion for Summary Judgment of noninfringement of all remaining claims [492] filed by defendant Alaris Medical Systems, Inc., dated on Sep. 29, 2006, Filed in Case No. SA CV 04-0689.

Declaration of Janice F. McCampbell in support of Motion for Summary Judgment of noninfringement of all remaining claims [492] filed by defendant Alaris Medical Systems, Inc., dated on Sep. 29, 2006, Filed in Case No. SA CV 04-0689.

Declaration of Kimberly N. Van Voorhis in support of opposition of Motion for Summary Judgment of invalidity of Spike-Less claims under 35 USC 112 [484] filed by plaintiff ICU Medical, Inc., dated Oct. 2, 2006, Filed in Case No. SA CV 04-0689.

Declaration of Bob Rogers in support of opposition of Motion for Summary Judgment of invalidity of Spike-Less claims under 35 USC 112 [484] filed by plaintiff Icu Medical, Inc., dated Oct. 2, 2006, Filed in Case No. SA CV 04-0689.

Plaintiff ICU Medical, Inc.'s Statement of genuine issues in opposition to Alaris's Motion for Summary Judgment of invalidity of Spike-Less claims under 35 USC 112 [484], Filed in Case No. SA CV 04-0689, dated Oct. 2, 2006.

Plaintiffs Opposition to Motion for Summary Judgment of noninfringement of all remaining claims [492], Filed in Case No. SA CV 04-0689, dated Oct. 26, 2006, public redacted version.

Declaration of Dr. Maureen Reitman in support of ICU opposition to Motion for Summary Judgment of noninfringement of all remaining claims [492], filed by plaintiff ICU Medical, Inc., Filed in Case No. SA CV 04-0689, dated Oct. 26, 2006.

Declaration of S. Christian Platt in opposition to Motion for Summary Judgment of noninfringement of all remaining claims [492] filed by plaintiff ICU Medical, Inc., Filed in Case No. SA CV 04-0689, dated Oct. 26, 2006.

Declaration of Neil Sheehan in support of Alaris Reply regarding its Motion for summary judgment of invalidity for lack of written description and certain exhibits to declaration [504] filed by defendant Alaris Medical Systems, Inc., Filed in Case No. SA CV 04-0689, dated Nov. 2, 2006.

Declaration of David D. Headrick in support Alaris Reply Memorandum in support of its Motion for Summary Judgment of noninfringement of all remaining claims [492] filed by Alaris Medical Systems, Inc., Filed in Case No. SA CV 04-0689, dated Nov. 2, 2006.

Defendant Alaris Medical Systems, Inc.'s Reply in support of Motion for Summary Judgment of invalidity of Spike-Less claims under 35 USC 112 [484], Filed in Case No. SA CV 04-0689, dated Nov. 2, 2006.

Plaintiff ICU Medical, Inc.'s Notice of recent decision on Alaris pending motion for summary judgment of noninfringement, Filed in Case No. SA CV 04-0689, dated Nov. 21, 2006.

Minutes of in Chambers Order held before Judge Mariana R. Pfaelzer, Filed in Case No. SA CV 04-0689, dated Dec. 4, 2006.

Supplemental Brief in Opposition to Notice of Motion and Motion for Summary Judgment of invalidity of Spike-Less claim under 35 USC 112 [484] filed by plaintiff, counter defendant Icu Medical Inc., Filed in Case No. SA CV 04-0689, dated Dec. 18, 2006.

Supplemental Declaration of S. Christian Platt support of Supplemental Brief in opposition to Notice of Motion and Motion for Summary Judgment of invalidity of Spike-Less claims under 35 USC 112 [484] filed by plaintiff, counter defendant ICU Medical, Inc., Filed in Case No. SA CV 04-0689, dated Dec. 18, 2006.

Defendant Alaris Medical Systems, Inc.'s Supplemental Brief in support of Notice of Motion and Motion for Summary Judgment of invalidity of Spike-Less claims under 35 USC 112 [484], Filed in Case No. SA CV 04-0689, dated Dec. 27, 2006.

Defendant Alaris Medical Systems, Inc.'s Second Supplemental Declaration of Scott P. McBride in support of Notice of Motion and Motion for Summary Judgment of invalidity of Spike-Less claims under 35 USC 112 [484], Filed in Case No. SA CV 04-0689, dated Dec. 27, 2006.

Notice of Motions and Motion in Limine, Filed in Case No. SA CV 04-0689. Motions include: #1. ICU Medical, Inc.'s Motion in Limine to exclude evidence and argument regarding prior motions and rulings; 2. ICU Medical, Inc.'s Motion in Limine to exclude evidence and argument regarding claim construction proceedings; 3. ICU Medical, Inc.'s Motion in Limine to exclude evidence and argument regarding regarding the *Medex* v. *ICU Medical, Inc.* Litigation; 4. ICU Medical, Inc.'s Motion in Limine to exclude evidence and argument regarding patent claims no longer in the case; 5. ICU Medical, Inc.'s Motion in Limine to exclude evidence and argument regardingSmartSite patenst and awards; 6. ICU Medical, Inc.'s Motion in Limine to exclude evidence and argument regarding ICU Medical, Inc.'s abandoned 1996 application and "regards as his invention" defense; 7. ICU Medical, Inc.'s Motion in Limine to exclude evidence and argument regarding ICU Medical, Inc.'s alleged "copying" of the SmartSite; 8. ICU Medical, Inc.'s Motion in Limine to exclude evidence and argument regarding delay in prosecution or litigation; 9. Alaris' inequitable conduct defense; 10. ICU Medical, Inc.'s Motion in Limine to exclude evidence and argument regarding Alaris' best mode defense; 11. ICU Medical, Inc.'s Motion in Limine to exclude evidence contrary to requests deemed admitted, dated Jan. 17, 2007.

Declaration of Kimberly N. Van Voorhis in support of Motions in Limine [643] filed by ICU Medical, Inc., Filed in Case No. SA CV 04-0689, dated Jan. 17, 2007.

Notice of Motions and Motions in Limine #1-12 to Preclude evidence and testimony [654] set for hearing Feb. 7, 2007 10:00 filed by defendants Alaris Medical Systems, Inc., Filed in Case No. SA CV 04-0689, dated Jan. 17, 2007.

Declaration of David D. Headrick in support re Motions in Limine #1-12 to Preclude evidence and testimony [654] filed by defendants Alaris Medical Systems, Inc., Filed in Case No. SA CV 04-0689, dated Jan. 17, 2007.

Order Granting [484] defendant Alaris Medical Systems, Inc. Motion for Summary Judgment of invalidity of Spike-Less claims and denying as moot [492] defendant Alaris Medical Systems, Inc. Motion for Summary Judgment of noninfringement of all remaining claims by Judge Mariana R. Pfaelzer, Filed in Case No. SA CV 04-0689, dated Jan. 22, 2007.

Minutes of in Chambers Order held before Judge Mariana R. Pfaelzer, Filed in Case No. SA CV 04-0689, dated Jan. 23, 2007.

Plaintiff ICU Medical, Inc.'s Notice of Errata regarding ICU's objection to Alaris proposed judgment of invalidity, Filed in Case No. SA CV 04-0689, dated Feb. 20, 2007.

Findings of Fact Not Genuinely Contested and Conclusions of Law in Support of the Court's Jan. 22, 2007 Order granting Alaris's motion for summary judgment of invalidity of Spikeless claims under 35 USC 112, paragraphs 1 and 2, Filed in Case No. SA CV 04-0689, dated Feb. 21, 2007.

Judgment of invalidity of Plaintiff ICU's Spikeless claims fewer than 35 USC 112 paragraphs 1 and 2, in favor of defendant Alaris Medical Systems, Inc. And against plaintiff ICU Medical, Inc. Claims 11-16 of U.S. Appl. No. 6,682,509 and claims 17-26, 31-42 and 46 of U.S. Appln. No. 6,572,592 are Invalid for lack of sufficient written description as required by 35 USC 112 first paragraph and for failing to claim the subject matter that their applicant Dr. George a. Lopez, regard as his invention in 1992, as is required by 35 USC 112, second paragraph; Plaintiff ICU's amended complaint is hereby Dismissed With Prejudice by Judge Mariana R. Pfaelzer; Related to: Alaris Motion for Summary Judgment of invalidity of Spike-Less Claims [136] (MD JS-6, Case Terminated), Filed in Case No. SA CV 04-0689, dated Feb. 21, 2007.

Judgment: In accordance with this court's Aug. 24, 2006, order, Alaris is Adjudged not to have infringed, either literally or under the doctrine of equivalents: (1) claims 1, 3-4 and 6-7 of U.S. Appln. No. 5,685,866, (2) claims 1 and 2 of U.S. Appln. No. 5,873,862, and (3) claims 11, 12 and 16 of U.S. Appln. No. 6,682,509, and (2) claims 17-26, 31-42 and 46 of the non-taxable costs in the amount of $4,978,343.93, with post-judgment interest to accrue in accordance with the Jun. 28, 2007 award by Judge Mariana R. Pfaelzer, in favor of Alaris Medical Systems, Inc. against ICU Medical, Inc. (MD JS-6, Case Terminated)., Filed in Case No. SA CV 04-0689, dated Sep. 21, 2007.

Stipulation and Order by Judge Mariana R. Pfaelzer that the Court supplements the Jun. 28, 2007 788, award of Alaris' fees and non-taxable costs and awards an additional $226,000 in fees and non-taxable costs to Defendant Alaris Medical Systems, Inc. The remaining counterclaims of Defendant Alaris Medical Systems, Inc., against Plaintiff ICU Medical, Inc., in the case are hereby dismissed without prejudice.  Filed NUNC PRO TUNC as of Sep. 21, 2007, Filed in Case No. SA CV 04-0689, dated Oct. 18, 2007.

ICU Medical, Inc's Notice of Appeal to Federal Circuit Court filed by Plaintiff ICU Medical, Inc. Filed in Case No. SA CV 04-0689 on Oct. 26, 2007, dated Oct. 24, 2007.

ICU Medical, Inc's Brief for Plaintiff-Appellant, Filed in Filed in Case No. SA CV 04-0689, dated Mar. 20, 2008.

Corrected Non-Confidential Brief for Defendant-Appellee Alaris Medical Systems, Inc., Filed in Case No. SA CV 04-0689, dated Jul. 2, 2008.

ICU Medical, Inc.'s Reply Brief, Filed in Case No. SA CV 04-0689, dated Jul. 25, 2008.

Joint Appendix vols. 1-3, Filed in Case No. SA CV 04-0689 on Aug. 1, 2008.

ICU Medical, Inc. 's Response to Alaris Medical System's Fifth Set of Interrogatories No. 16, Filed in Case No. SA CV 04-0689, dated May 31, 2006, public redacted version.

Verification of Francis J. O'Brien in Support of ICU Medical, Inc.'s Response to Alaris Medical System's 5th Set of Interrogatories No. 16, Filed in Case No. SA CV 04-0689, dated May 31, 2006.

ICU Medical, Inc.'s Supplemental Response to Alaris Medical System's Fifth Set of Interrogatories No. 16, Filed in Case No. SA CV 04-0689, dated Jun. 29, 2006, public redacted version.

ICU Medical, Inc.'s Second Supplemental Responses to Alaris Medical System's Fifth Set of Interrogatories No. 13 (Third Set), Filed in Case No. SA CV 04-0689, dated Jul. 12, 2006, public redacted version.

U.S. District Court Civil Docket for *ICU Medical, Inc.* v. *Rymed Technologies, Inc.,* Case No. 1:07- cv-00468-JJF, dated Aug. 22, 2008.

Complaint filed with Jury Demand against RyMed Technologies, Inc. By ICU Medical, Inc. filed in Case No. 1:07-cv-00468-JJF, dated Jul. 27, 2007.

Answer to Complaint with Jury Demand, Counterclaim against ICU Medical, Inc. by RyMed Technologies, Inc., Filed in Case No. 1:07-cv-00468-JJF, dated Oct. 12, 2007.

Answer to Counterclaim [Plaintiff ICU Medical, Inc.'s Reply to RyMed Technologies, Inc.'s Counterclaims with Defenses], filed in Case No. 1:07-cv-00468-JJF, dated Nov. 1, 2007.

U.S. District Court Civil Docket for *Rymed Technologies, Inc.* v. *ICU Medical, Inc.,* Case No. 8:07- cv-01199-MRP-VBK, dated Aug. 20, 2008.

Complaint filed by Rymed Technologies against ICU Medical including Report on the filing of an Action regarding a Patent, Civil Cover Sheet, Summons, Notice of Related Cases, and Notice of Interested Parties in Case no. 8:07-cv-01199-MRP-VBK, dated Oct. 10, 2007.

Answer to Counterclaim [Plaintiff ICU Medical, Inc.'s Reply to RyMed Technologies, Inc.'s Counterclaims with Defenses], filed in Case No. 8:07-cv-01199-MRP-VBK, dated Jun. 5, 2008.

Answer to Counterclaim [Defendant RyMed Technologies, Inc.'s Reply to Plaintiff ICU Medical, Inc.'s Counterclaims with Defenses], filed in Case No. 8:07-cv-01199-MRP-VBK, dated Jun. 30, 2008.

U. S. Court of Appeals for the Federal Circuit, *ICU Medical, Inc.* v. *Alaris Medical,* Docket No. 2008-1077, Transcript of Oral Argument dated Jan. 5, 2009.

U. S. Court of Appeals for the Federal Circuit, *ICU Medical, Inc.* v. *Alaris Medical,* Docket No. 2008-1077, Opinion dated Mar. 13, 2009.

U.S. Appl. No. 07/813,073, filed Dec. 18, 1991, including its prosecution history, including office communications dated Jul. 23 and 30, 1992, and Apr. 19, 1993.

U.S. Appl. No. 08/475,595, filed Jun. 7, 1995, including its prosecution history, including office communications dated Jun. 4, 1996, May 2, 1997, and Dec. 8, 1997.

U.S. Appl. No. 08/475,599, filed Jun. 7, 1995, including its prosecution history, including office communications dated May 31, 1996, and Sep. 9, 1997.

U.S. Appl. No. 08/479,681, filed Jun. 7, 1995, including its prosecution history, including office communications dated Dec. 16, 1996, Jun. 13, 1996, Mar. 11, 1997, and Nov. 11, 1997.

U.S. Appl. No. 08/905,370, filed Aug. 4, 1997, including its ongoing prosecution history, including office communications dated Feb. 24, 1998, Sep. 30, 1998, Nov. 9, 1999, and Jun. 13, 2000.

U.S. Appl. No. 10/630,131, filed Jul 30, 2003, published as US2004-0073174, on Apr. 15, 2004, including its ongoing prosecution history, including office communications dated Feb. 25, 2005, Oct. 13, 2006, and May 1, 2007.

U.S. Appl. No. 10/882,469, filed Jul. 1, 2004, published as US2004-0243070 A1, on Dec. 2, 2004, including its ongoing prosecution history, including office communications dated Nov. 13, 2007, Mar. 18, 2008, and Feb. 5, 2009.

U.S. Appl. No. 08/265,095, filed Jun. 24, 1994, including its prosecution history, including office communications dated Jul. 17, 1995, Mar. 8, 1996, Oct. 9, 1996, and Apr. 29, 1997.

*ICU Medical, Inc.* v. *Rymed Technologies, Inc.,* Case No. 07-468-JJF in the USDC for The District of Delaware, Excerpts of Deposition of Alison Burcar, vol. I, Jun. 12, 2009, (including Excerpts of Exhibits).

*ICU Medical, Inc.* v. *Rymed Technologies, Inc.,* Case No. 07-468-JJF in the USDC for The District of Delaware, Excerpts of Deposition of Alison Burcar, vol. II, Jun. 25, 2009, (including Excerpts of Exhibits).

*ICU Medical, Inc.* v. *Rymed Technologies, Inc.,* Case No. 07-468-JJF in the USDC for The District of Delaware, Excerpts of Deposition of John Keener, Jun. 19, 2009, (including Excerpts of Exhibits).

*ICU Medical, Inc.* v. *Rymed Technologies, Inc.,* Case No. 07-468-JJF in the USDC for The District of Delaware, Excerpts of Deposition of Jean M. Bonaldo, vol. I, Jun. 16, 2009, (including Excerpts of Exhibits).

*ICU Medical, Inc.* v. *Rymed Technologies, Inc.,* Case No. 07-468-JJF in the USDC for The District of Delaware, Excerpts of Deposition of Jean M. Bonaldo, vol. II, Jun. 26, 2009, (including Excerpts of Exhibits).

*ICU Medical, Inc.* v. *Rymed Technologies, Inc.,* Case No. 07-468-JJF in the USDC for The District of Delaware, Excerpts of Deposition of George Lopez, vol. I, Jun. 23, 2009, (including Excerpts of Exhibits).

*ICU Medical, Inc.* v. *Rymed Technologies, Inc.,* Case No. 07-468-JJF in the USDC for The District of Delaware, Excerpts of Deposition of George Lopez, vol. II, Jun. 24, 2009, (including Excerpts of Exhibits).

*ICU Medical, Inc.* v. *Rymed Technologies, Inc.,* Case No. 07-468-JJF in the USDC for The District of Delaware, Excerpts of Deposition of Steven J. Nataupsky, Jun. 10, 2009, (including Excerpts of Exhibits).

*ICU Medical, Inc.* v. *Rymed Technologies, Inc.,* Case No. 07-468-JJF in the USDC for The District of Delaware, Defendant Rymed Technologies, Inc.'s Opening Claim Construction Brief, May 15, 2009.

*ICU Medical, Inc.* v. *Rymed Technologies, Inc.,* Case No. 07-468-JJF in the USDC for The District of Delaware, Declaration of Claude Vidal in Support of ICU's Opening Claim Construction Brief, May 15, 2009.

*ICU Medical, Inc.* v. *Rymed Technologies, Inc.,* Case No. 07-468-JJF in the USDC for The District of Delaware, Declaration of Irene Yang in Support of Defendant Rymed Technologies, Inc.'s Opening Claim Construction Brief, May 15, 2009, (including Exhibits).

*ICU Medical, Inc.* v. *Rymed Technologies, Inc.,* Case No. 07-468-JJF in the USDC for The District of Delaware, ICU Medical, Inc.'s Opening Claim Construction Brief, May 15, 2009.

*ICU Medical, Inc.* v. *Rymed Technologies, Inc.*, Case No. 07-468-JJF in the USDC for The District of Delaware, Declaration of Kimberly N. Van Voorhis in Support of ICU Medical, Inc.'s Opening Claim Construction Brief, May 15, 2009, (including Exhibits).
*ICU Medical, Inc.* v. *Rymed Technologies, Inc.*, Case No. 07-468-JJF in the USDC for The District of Delaware, Defendant Rymed Technologies, Inc.'s Answering Claim Construction Brief, Jun. 15, 2009.
*ICU Medical, Inc.* v. *Rymed Technologies, Inc.*, Case No. 07-468-JJF in the USDC for The District of Delaware, Declaration of Edward E. Elson in Support of Defendant Rymed Technologies, Inc.'s Answering Claim Construction Brief, Jun. 15, 2009.
*ICU Medical, Inc.* v. *Rymed Technologies, Inc.*, Case No. 07-468-JJF in the USDC for The District of Delaware, ICU Medical, Inc.'s Answering Claim Construction Brief, Jun. 15, 2009.
*ICU Medical, Inc.* v. *Rymed Technologies, Inc.*, Case No. 07-468-JJF in the USDC for The District of Delaware, Declaration of Claude Vidal in Support of ICU's Answering Claim Construction Brief, Jun. 15, 2009, (including Exhibits).
*ICU Medical, Inc.* v. *Rymed Technologies, Inc.*, Case No. 07-468-JJF in the USDC for The District of Delaware, Declaration of Kimberly N. Van Voorhis in Support of ICU Medical, Inc.'s Answering Claim Construction Brief, Jun. 15, 2009, (including Exhibits).
*ICU Medical, Inc.* v. *Rymed Technologies, Inc.*, Case No. 07-468-JJF in the USDC for The District of Delaware, Defendant Rymed Technologies, Inc.'s Supplemental Objections and Responses to Plaintiff ICU Medical, Inc.'s Interrogatory Nos. 3 and 4, Nov. 3, 2008.
*ICU Medical, Inc.* v. *Rymed Technologies, Inc.*, Case No. 07-468-JJF in the USDC for The District of Delaware, Rymed Technologies, Inc.'s Fourth Supplemental Objections and Responses to ICU Medical, Inc.'s First Set of Interrogatories, Jun. 17, 2009.
*ICU Medical, Inc.* v. *Rymed Technologies, Inc.*, Case No. 07-468-JJF in the USDC for The District of Delaware, Rymed Technologies, Inc.'s Fifth Supplemental Objections and Responses to ICU Medical, Inc.'s First Set of Interrogatories, Jun. 22, 2009.
*ICU Medical, Inc.* v. *Rymed Technologies, Inc.*, Case No. 07-468-JJF in the USDC for The District of Delaware, Defendant Rymed Technologies, Inc.'s Amended Answer to ICU Medical, Inc.'s Complaint for Patent Infringement, Defenses, and Counter-Plaintiff Rymed's Counterclaims, Apr. 17, 2009.
*ICU Medical, Inc.* v. *Rymed Technologies, Inc.*, Case No. 07-468-JJF in the USDC for The District of Delaware, Plaintiff ICU Medical, Inc.'s Reply to Rymed's Amended Answer to ICU Medical, Inc.'s Complaint and Counter-Plaintiff Rymed's Counterclaims, May 4, 2009.
*ICU Medical, Inc.* v. *Alaris Medical Systems, Inc.*, Case No. 04-CV-0689 in the USDC for The District of California, Plaintiff ICU Medical, Inc.'s Petition for Panel Rehearing, Mar. 26, 2009.
*ICU Medical, Inc.* v. *Alaris Medical Systems, Inc.*, Case No. 04-CV-0689 in the USDC for The District of California, Order Denying ICU Medical, Inc.'s Petition for Panel Rehearing, Apr. 8, 2009.
*ICU Medical, Inc.* vs. *Rymed Technologies, Inc.*, Case No. 07-468-JJF in the USDC for The District of Delaware, Markman Hearing Transcript, Sep. 9, 2009.
*ICU Medical, Inc.* v. *Rymed Technologies, Inc.*, Case No. 07-468-JJF in the USDC for The District of Delaware, Declaration of George Kipe, Nov. 2009 (including Exhibit).
*ICU Medical, Inc.* v. *Rymed Technologies, Inc.*, Case No. 07-468-JJF in the USDC for The District of Delaware, Motion in Limine No. 3 to Preclude Defendant From Referencing Invalid Claims of the '592 Patent and the Attorneys' Fees Award Against ICU in the *Alaris* Litigation, Nov. 24, 2009.
*ICU Medical, Inc.* v. *Rymed Technologies, Inc.*, Case No. 07-468-JJF in the USDC for The District of Delaware, Declaration of Mark Gaona, Dec. 1, 2009.
*ICU Medical, Inc.* v. *Rymed Technologies, Inc.*, Case No. 07-468-JJF in the USDC for The District of Delaware, Declaration of Harold Anderson, Dec. 1, 2009.
*ICU Medical, Inc.* v. *Rymed Technologies, Inc.*, Case No. 07-468-JJF in the USDC for The District of Delaware, Declaration of Dennis Bui, Oct. 1, 2009 (including Exhibits).
*ICU Medical, Inc.* v. *Rymed Technologies, Inc.*, Case No. 07-468-JJF in the USDC for The District of Delaware, Markman Memorandum Opinion and Order, Dec. 3, 2009.
*ICU Medical, Inc.* v. *Rymed Technologies, Inc.*, Case No. 07-468-JJF in the USDC for The District of Delaware, ICU Medical, Inc.'s Motion in Limine No. 5 regarding Rymed's "Inventorship" Claim as to Messrs. Bui, Duffield, Mayer and Kipe, Dec. 4, 2009.
*ICU Medical, Inc.* v. *Rymed Technologies, Inc.*, Case No. 07-468-JJF in the USDC for The District of Delaware, ICU Medical, Inc.'s Motion in Limine No. 6 regarding Exclusion of Evidence regarding Jean Bonaldo and Related Defenses, Dec. 4, 2009.
*ICU Medical, Inc.* v. *Rymed Technologies, Inc.*, Case No. 07-468-JJF in the USDC for The District of Delaware, Deposition of Dennis Bui, Dec. 10, 2009 (including Exhibits).
*ICU Medical, Inc.* v. *Rymed Technologies, Inc.*, Case No. 07-468-JJF in the USDC for The District of Delaware, ICU Medical, Inc.'s Reply in Support of Motion in Limine No. 3 to Exclude Evidence relating to Invalid '592 Patent Claims and the Attorneys' Fees Award Against ICU in the *Alaris* Litigation, Dec. 14, 2009.
*ICU Medical, Inc.* v. *Rymed Technologies, Inc.*, Case No. 07-468-JJF in the USDC for The District of Delaware, Memorandum Opinion in regard to Rymed Technologies, Inc.'s Motion to Modify Scheduling Order and for Leave to File Second Amended Answer to ICU Medical, Inc.'s Complaint for Patent Infringement, Defenses, and Counter-Plaintiff Rymed's Counterclaims; and ICU Medical, Inc.'s Motion for Leave to File Sur-Reply, Dec. 16, 2009.
*ICU Medical, Inc.* v. *Rymed Technologies, Inc.*, Case No. 07-468-JJF in the USDC for The District of Delaware, ICU Medical, Inc.'s Reply in Support of Motion in Limine No. 4 regarding Evidence Comparing the Clave/Microclave to the Invision-Plus, Dec. 21, 2009.
*ICU Medical, Inc.* v. *Rymed Technologies, Inc.*, Case No. 07-468-JJF in the USDC for The District of Delaware, ICU Medical, Inc.'s Reply in Support of Motion in Limine No. 5 regarding Rymed's "Inventorship" Claim as to Messrs. Bui, Duffield, Mayer and Kipe, Dec. 21, 2009.
*ICU Medical, Inc.* v. *Rymed Technologies, Inc.*, Case No. 07-468-JJF in the USDC for The District of Delaware, ICU Medical, Inc.'s Reply in Support of Motion in Limine No. 6 regarding Exclusion of Evidence regarding Jean Bonaldo and Related Defenses, Dec. 21, 2009.
*ICU Medical, Inc.* v. *Rymed Technologies, Inc.*, Case No. 07-468-JJF in the USDC for The District of Delaware, Rymed's Opposition to ICU Motion in Limine No. 6 relating to the Inventorship Issues Raised by the Inventors of Jean Bonaldo, Redacted Version filed Jan. 13, 2010 (Exhibits A-F are redacted in their entirety).
*ICU Medical, Inc.* v. *Rymed Technologies, Inc.*, Case No. 07-468-JJF in the USDC for The District of Delaware, Rymed's Opposition to ICU Motion in Limine No. 5 relating to the Inventorship Issues Raised by the Contributions of Messrs. Bui, Duffield, Mayer and Kipe, Redacted Version filed Jan. 13, 2010 (with Exhibits, Exhibits A-B and D-E are redacted in their entirety).
*ICU Medical, Inc.* v. *Rymed Technologies, Inc.*, Case No. 07-468-JJF in the USDC for The District of Delaware, Rymed's Opposition to ICU Motion in Limine No. 4 regarding Evidence Comparing the Clave/Microclave to Invision Plus, Redacted Version filed Jan. 13, 2010 (Exhibits A-C are redacted in their entirety).
*ICU Medical, Inc.* v. *Rymed Technologies, Inc.*, Case No. 07-468-JJF in the USDC for The District of Delaware, Rymed's Opposition to ICU Motion in Limine No. 3 regarding Invalid Claims of the '592 Patent and the Attorneys' Fees Award Against ICU in the *Alaris* Litigation, Redacted Version filed Jan. 13, 2010 (with Exhibits, Exhibit C is redacted in its entirety).
*ICU Medical, Inc.* v. *Rymed Technologies, Inc.*, Case No. 07-468-JJF in the USDC for The District of Delaware, Rymed's Opposition to ICU Motion in Limine No. 2 regarding Prior ICU Patent Litigation, Redacted Version filed Jan. 13, 2010 (with Exhibits).
*ICU Medical, Inc.* v. *Rymed Technologies, Inc.*, Case No. 07-468-JJF in the USDC for The District of Delaware, Rymed's Opposition to ICU Motion in Limine No. 1 to Limit the Trial Testimony of Defendant's Experts to Matters Disclosed in Their Written Expert Reports, Redacted Version filed Jan. 13, 2010 (Exhibits A-C are redacted in their entirety).
Office Communication dated Feb. 24, 2010 in U.S. Appl. No. 11/417,642, filed May 3, 2006.
Office Communication dated Feb. 26, 2010 in U.S. Appl. No. 11/417,461, filed May 3, 2006.

Office Communication dated Mar. 2, 2010 in U.S. Appl. No. 11/417,700, filed May 3, 2006.
Office Communication dated Feb. 24, 2010 in U.S. Appl. No. 11/417,452, filed May 3, 2006.
Office Communication dated Mar. 11, 2010 in U.S. Appl. No. 11/417,713, filed May 3, 2006.
Office Communication dated Mar. 11, 2010 in U.S. Appl. No. 11/381,527, filed May 3, 2006.
Office Communication dated Mar. 1, 2010 in U.S. Appl. No. 11/381,524, filed May 3, 2006.
Office Communication dated Mar. 2, 2010 in U.S. Appl. No. 11/381,526, filed May 3, 2006.
Office Communication dated Feb. 26, 2010 in U.S. Appl. No. 11/417,669, filed May 3, 2006.

* cited by examiner

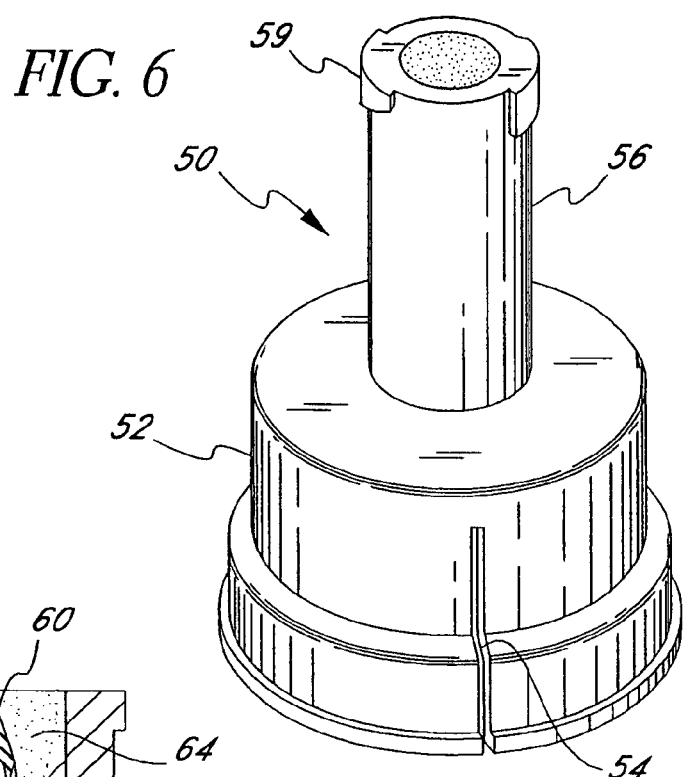
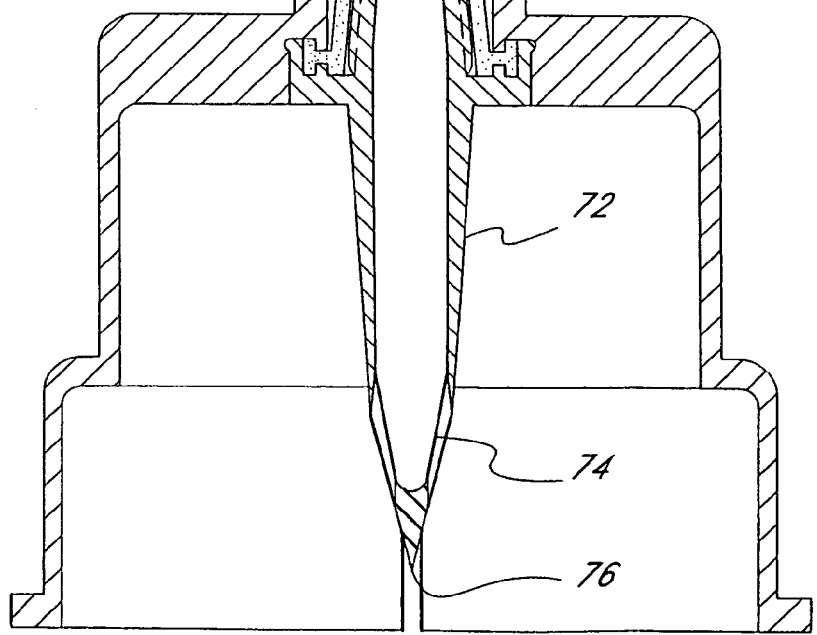
FIG. 6
FIG. 7

MEDICAL VALVE AND METHOD OF USE

CROSS-REFERENCE TO RELATED APPLICATIONS

This application is a continuation of U.S. application Ser. No. 10/630,131, filed Jul. 30, 2003, now abandoned, which is a continuation of U.S. application Ser. No. 10/163,403, filed Jun. 5, 2002, now U.S. Pat. No. 6,669,673 which was a continuation of U.S. application Ser. No. 09/569,712, filed May 9, 2000, now U.S. Pat. No. 6,572,592, which was a continuation of U.S. application Ser. No. 08/905,370, filed Aug. 4, 1997, now abandoned, which was a continuation of U.S. application Ser. No. 08/334,846, filed Nov. 4, 1994, now U.S. Pat. No. 5,685,866, which was a continuation of U.S. application Ser. No. 08/096,659, filed Jul. 23, 1993, now U.S. Pat. No. 5,695,466, which was a continuation-in-part of PCT Application No. PCT/US92/10367, filed Dec. 1, 1992, now abandoned, which was continuation-in-part of U.S. application Ser. No. 07/813,073, filed Dec. 18, 1991, now abandoned. This application incorporates by reference the above identified applications in their entireties.

BACKGROUND OF THE INVENTION

1. Field of the Invention

This invention relates to a closed, patient access system which automatically reseals after administering medication using a standard medical implement that directly connects with the system without the need of any intermediary needles, caps or adaptors. A two-way valve eliminating dead space is used which includes a seal which, upon being compressed by the medical implement, is pierced to open the valve and reseals upon being decompressed, maintaining a fluid tight seal even at high pressures and after repeated uses.

2. Description of the Related Art

The manipulation of fluids for parenteral administration in hospital and medical settings routinely involves the use of connectors and adaptors for facilitating the movement of fluids between two points. Most fluid connectors and adaptors employ needles to pierce a septum covering tubing or to pierce the septum of a medicament container of fluid. Fluid then passes from the container or fluid filled tubing into a syringe or second set of tubing. These connectors and adaptors often have mechanical or moving parts. Since the ready passage of fluids through the connectors and adaptors is often critical to patient survival, it is imperative that the connectors and adaptors function reliably and repeatedly. Adaptors and connectors that malfunction during use may be life-threatening. The more mechanical or moving parts such as springs and diaphragms, the more likely that they will function improperly. Improper functioning can result in the introduction of air embolisms into a patient. Thus, the fewer the mechanical parts, the more these connectors can be relied on and the better they will be accepted by the medical community.

Many connectors or valves, especially those employing several mechanical components, have a relatively high volume of fluid space within them. This "dead space" within the device prevents accurate introduction of precise fluid volumes and provides an opportunity for contamination upon disconnection of the device. Connectors and adaptors often include valves that permit or interrupt the flow of fluid along the course of fluid travel. Several of those commonly in use employ metal needles to puncture sterile seals. Such connectors are generally designed to accommodate fluid flow in one direction. This means that the fluid line must have connectors and tube aligned in complementary directions. These connectors often require further manipulation if, for example, the valve is inadvertently assembled in a direction that will not facilitate fluid flow. These manipulations increase handling, thereby increasing both the risk of contamination and the amount of time required to establish the fluid connection.

Metal needles employed as part of connector devices increase the risk of puncture wounds to the user. The needles used in these devices often have through-holes placed at the tip of the needle. Connection of the valve with a flow line involves piercing the needle through a sealed septum. Through-holes placed at the needle tip can core the septum and release free particulates into the flow line. Such an event can prove fatal to a patient. Such through-holes may also become clogged easily with material from the septum.

Reusable connectors and adaptors are preferred for medical applications since components must often be added or removed from a fluid line connected to a patient. Reusable connectors, however, are difficult to keep sterile. Sometimes caps are employed to cover the connector to keep it sterile. Frequently, these caps are lost, or simply not used because they are not readily available when needed.

A closed, patient access system that is easy to use and employs only a valve device in communication with the patient that need not be capped or interconnected with the medical implement through a needle or adaptor, is swabbable, is sufficiently durable to maintain its function after several manipulations, and maintains a fluid-tight seal at high pressures, would be of great benefit to the medical community.

SUMMARY OF THE INVENTION

The valve of this invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENTS," one will understand how the features of this invention provide its advantages, which include safety, reliable and repeatable performance, elimination of dead space, simplicity of manufacture and use, and employment of a valve that is swabbable after use to provide sterility and has a fluid-tight seal at high pressure.

This invention is a closed, patient access system which automatically reseals after administering medication using a medical implement that directly connects with the system without the need of any intermediate needles, caps or adaptors. A two-way valve is employed utilizing a reusable seal that may be repeatedly pierced by an enclosed, protected, non-metallic spike rather than an exposed metal needle. The valve facilitates fluid, particularly liquid, transfer while maintaining sterility. The valve is easy to use and is capable of locking in place. After use, the valve is swabbed in the conventional manner with a suitable substance to maintain sterility. The design of the valve avoids accidental needle sticks. As will be discussed in detail below, the valve is useful as a medical connector or adaptor to enable liquid flow from a sealed container.

The first feature of this invention in that the valve has a body including wall structure defining an internal cavity having a proximal end and a distal end. The cavity has an open space into which the seal is pushed, and preferably has a plurality of radial indentations in the wall structure that are adjacent the seal to accommodate the expansion of the seal upon compression. The proximal end has an opening sufficiently large to receive a delivery end of a medical implement which transfers fluid through the delivery end. In most applications, the delivery end of the implement is tapered, and the wall structure adjacent the opening is tapered inward so that the wall structure and the tapered delivery end fit snug against each other upon insertion of the delivery end into the opening. The proximal end of the cavity preferably is adapted to fit snug with an ANSI (American National Standards Institute, Washington, D.C.) standard end of the medical implement. Typically, the implement is a syringe, a connector or inlet/outlet of an IV set, or any one of a wide variety of conduits used in medical applications.

The second feature is that the spike has a tip with at least one hole located at or near the tip, and a passageway in communication with the hole that allows fluid to flow through this hole. The spike is seated inside the cavity such that the tip is inward of the proximal end and is enclosed within the cavity. Preferably, the hole is in a side of the spike adjacent the tip and is elongated, having a size of 18 gauge or greater. The tip may be sharp or slightly rounded. More than one hole is desirable for many applications, and three, symmetrically located holes inward of the proximal end are preferred. The spike may include at least one rib which allows air to enter a space between the seal and the spike, thereby facilitating the sealing of the opening when the implement is removed. The spike may have a substantially conical shape, and the seal has a complementarily, substantially conical shaped cavity within it conforming to the shape of the spike. The spike is disposed within this conical cavity and the seal covers the tip. The tip may be imbedded in the proximal end of the seal or withdrawn into the conical cavity. Preferably, the tip of the spike has a plurality of facets which meet within a recess. The preferred spike should be able to penetrate the seal repeatedly without tearing the seal. Rough edges at the tip may present a tear problem. During injection molding of the preferred plastic spike, facets of the tip will abut along a "parting line," and could form a rough edge which may tear the seal. This problem is avoided where the parting line is buried in a recess. Any rough edge at this parting line is disposed within a recess, so the seal material moves over the recess and does not contact the rough edge.

The third feature is that the resilient seal is adapted to be moved into a compressed state upon insertion of the tip of the medial implement into the opening and returns to a decompressed state upon removal of the tip. The seal in the decompressed state has a section which fills essentially completely a portion of the cavity adjacent the opening. The seal section bears against the wall structure near the opening to seal the opening. In the compressed state, the seal section is pushed by the delivery end of the medical implement away from the opening and into the cavity. A fluid tight seal is maintained between the seal section and the wall structure as the seal is moved into the compressed state. The seal section bears against the wall structure as the seal is moved inward into the cavity by the tip of the medical implement. And most importantly, the delivery end and the seal are adapted to engage so that when the tip of the spike pierces the seal there is essentially no dead space between said delivery end and the seal. Consequently, a predetermined dosage amount of medication is transferred in its entirety to the patient using this invention, with none to the prescribed amount being collected in dead space in the valve. The delivery of an exact amount of medication may be critical in some situations when chemotherapeutic agents are being administered or small children are being treated.

A fluid tight seal is maintained over repeated opening and closing of the valve, and the seal has on its external surface a recess which provides an air pocket to facilitate the movement of the seal. Preferably, the seal presents an essentially flush surface with the proximal end of the cavity. In one embodiment, the proximal end of the seal is substantially flat, the seal is made of a material having a hardness of from 30 to 70 Shore units such as, for example, a silicone polymer. The seal may include a cup-like flange adapted to engage the body near the proximal end of the cavity. A preferred embodiment of the seal comprises of a series of O-ring elements stacked together and connected to form a unitary structure. The O-ring elements have increasing diameters, with the smallest diameter element begin adjacent the proximal end of the cavity. The proximal end of the seal may be precut to form a tiny orifice therein that allows the tip of the spike to pass therethrough easily upon compression of the seal. Preferably, the proximal end of the seal has a truncated conical shaped segment disposed within the cavity. The seal may also have a centrally located, anti-vacuum, saucer like depression therein, which does not interfere with the ability of the exposed, proximal end of the seal being swabbed when desired.

The fourth feature is that the body and spike are two separate components of the valve that are securely attached to each other by assembly of, and interlocking, of the body and spike. The body has a first locking element near the distal end of the cavity, and the spike has a second locking element adapted to interlock with said first locking element upon assembly. The seal has a lip extending beyond the distal end and positioned between the first and second locking elements so that, upon assembly, the lip is compressed between the locking elements to provide an essentially fluid tight seal upon interlocking.

The fifth feature is that the medical valve includes a support member connected to the spike which seals off the distal end of the cavity. The support member may have a Luer-Lock type connector element that enables the valve to be removably attached to, for example, a fluid line connected to a patient. The support member may also be in the form of an adaptor that enables the valve to be removably attached to a fluid dispenser or container. When used to dispense fluids from a container, the spike has a pair of opposed tips, respectively at the distal and proximal ends of the spike. The tip at the distal end of the spike pierces a cover member which seals the container. A radial slit on the adaptor enables it to deform reversibly sufficiently to fit snugly onto said container.

The sixth feature is that the seal has a proximal end including a pressure responsive element disposed on an inner surface of the seal adjacent the opening. The pressure responsive element in the decompressed state closes any orifice in the seal at the proximal end of the seal to provide an essentially fluid-tight seal while in the decompressed state. The pressure responsive element enables the valve to maintain a fluid-tight seal even at very high pressures sometimes experienced in medical applications, particularly when the valve is connected to a patient's artery. The valve of this invention will remain closed even when the pressure inside the valve is above 6 pounds per square inch (psi), and it can withstand pressures above 30 psi. Typically, the pressure responsive element is a section of the seal having an entryway into a precut orifice. This section has a substantially cylindrical configuration and is surrounded by an annular space which is filled with pressurized fluid. The center of the member and the annular space are coaxial with the entryway to the orifice. The pressurized fluid fills the annular space to apply pressure that compresses the cylindrical section to tightly close the entryway to the orifice. Preferably, the pressure responsive element has an anti-tear element.

In accordance with this invention, a known, prescribed, predetermined amount or dosage of medication may be transferred from the remote source to the patient directly, so that essentially none of said predetermined amount is collected in dead space in the valve. In other words essentially all the prescribed dosage is received by the patient and not lost in the valve. Thus, this invention also includes a method of transferring fluid from a remote source to a patient. This invention also includes transfer of fluid from the patient to a remote source. This is possible because the valve of this invention provides two-way communication. The fluid is transferred to the patient by applying pressure to the fluid as it passes through the implement so that the pressure applied to the fluid is greater than the pressure of fluid in the patient, enabling transfer from the remote source to the patient. To achieve transfer of fluid from the patient to the remote source, the pressure of fluid in the patient is greater than the pressure at the remote source, causing fluid to flow from the patient to the remote source. This invention also includes a method of transferring fluid in a container having an open mouth covered by a cover member which seals the open mouth. The fluid is caused to flow from the container through the passageway by creating a differential in pressure. Preferably, the valve has an adaptor having a radial slit for allowing the adaptor to deform reversibly sufficiently to fit snugly onto said container.

BRIEF DESCRIPTION OF THE DRAWINGS

The preferred embodiments of this invention, illustrating all its features, will now be discussed in detail. These embodiments depict the novel and non-obvious method and valve of this invention shown in the accompanying drawing, which is for illustrative purposes only. This drawing includes the following Figures, with like numerals indicating like parts:

FIG. 6 is a perspective view of a second embodiment of the invention.

FIG. 7 is a longitudinal cross-sectional view of the valve of FIG. 6.

DETAILED DESCRIPTION OF THE PREFERRED EMBODIMENT

The term "proximal" is used to denote the end of the valve and other components at or near the spike tip 32 in FIGS. 2 through 5, 10 through 12, 14 and 16, and at or near the spike tip 60 in FIG. 6, and at or near the seal cap 92 in FIGS. 8, 9, 13 through 19. The term "distal" is used to denote the opposite end of the valve, or spike tip, or seal. The term "medical implement" is used to denote any medical tool known to those of skill in the art that can connect to the present invention and facilitate the passage of fluids, particularly liquids, through the instant invention. Examples of medical implements that are contemplated include, but are not limited to, tubing, conduit, syringes, IV sets (both peripheral and central lines), piggyback lines, and other components which can be used in connection with medical valve. Medical implements are commercially available in standard sizes. Thus, either or both ends of the valve of this invention can be provided with fittings to accommodate such standard size medical implements.

Figures 1, 2:
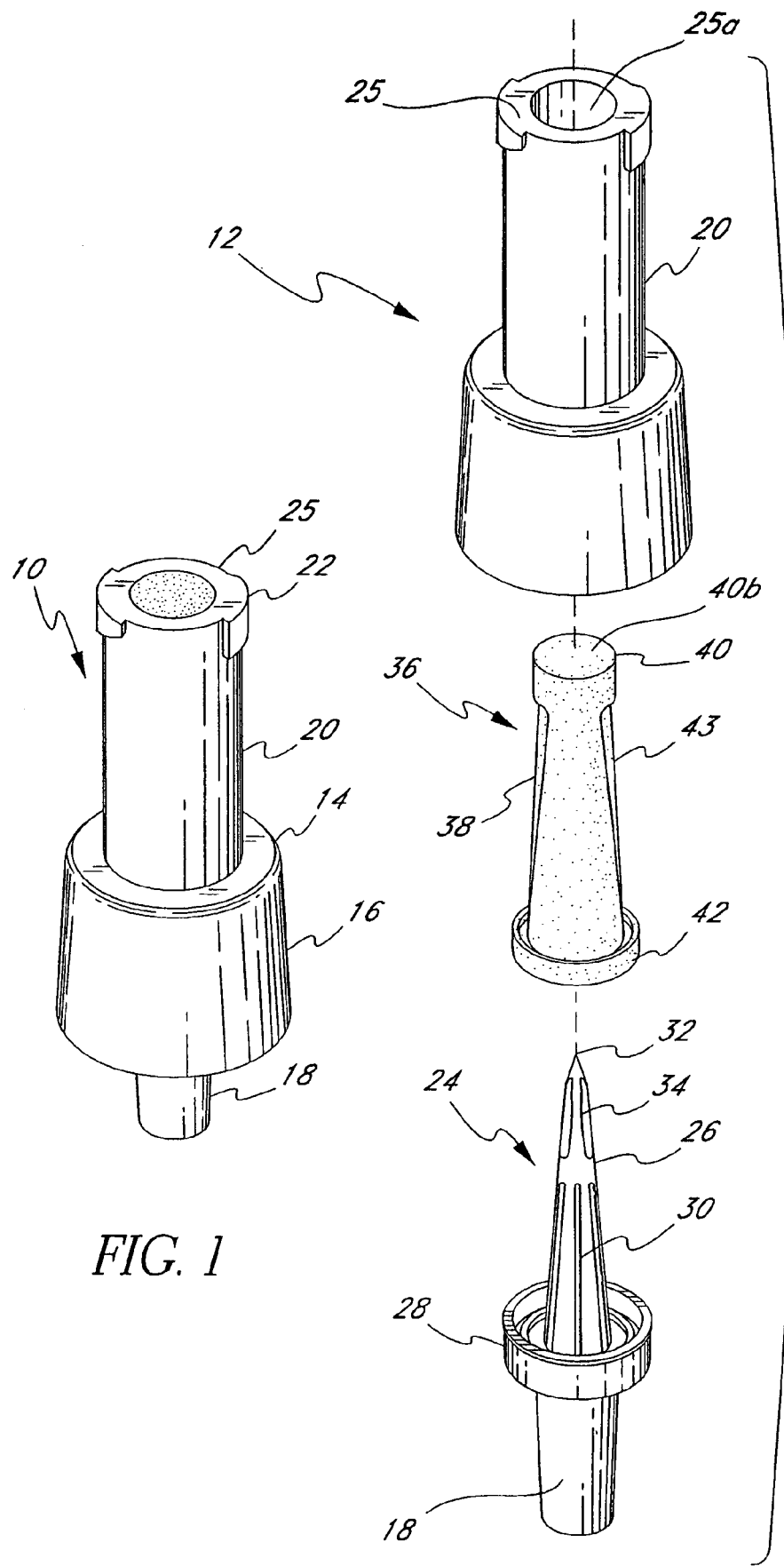
FIG. 1 is a perspective view of the first embodiment of the valve of this invention.
FIG. 2 is an exploded perspective view of the valve shown in FIG. 1 illustrating the spike, seal, and the body or housing components of the invention.
Figure 3:
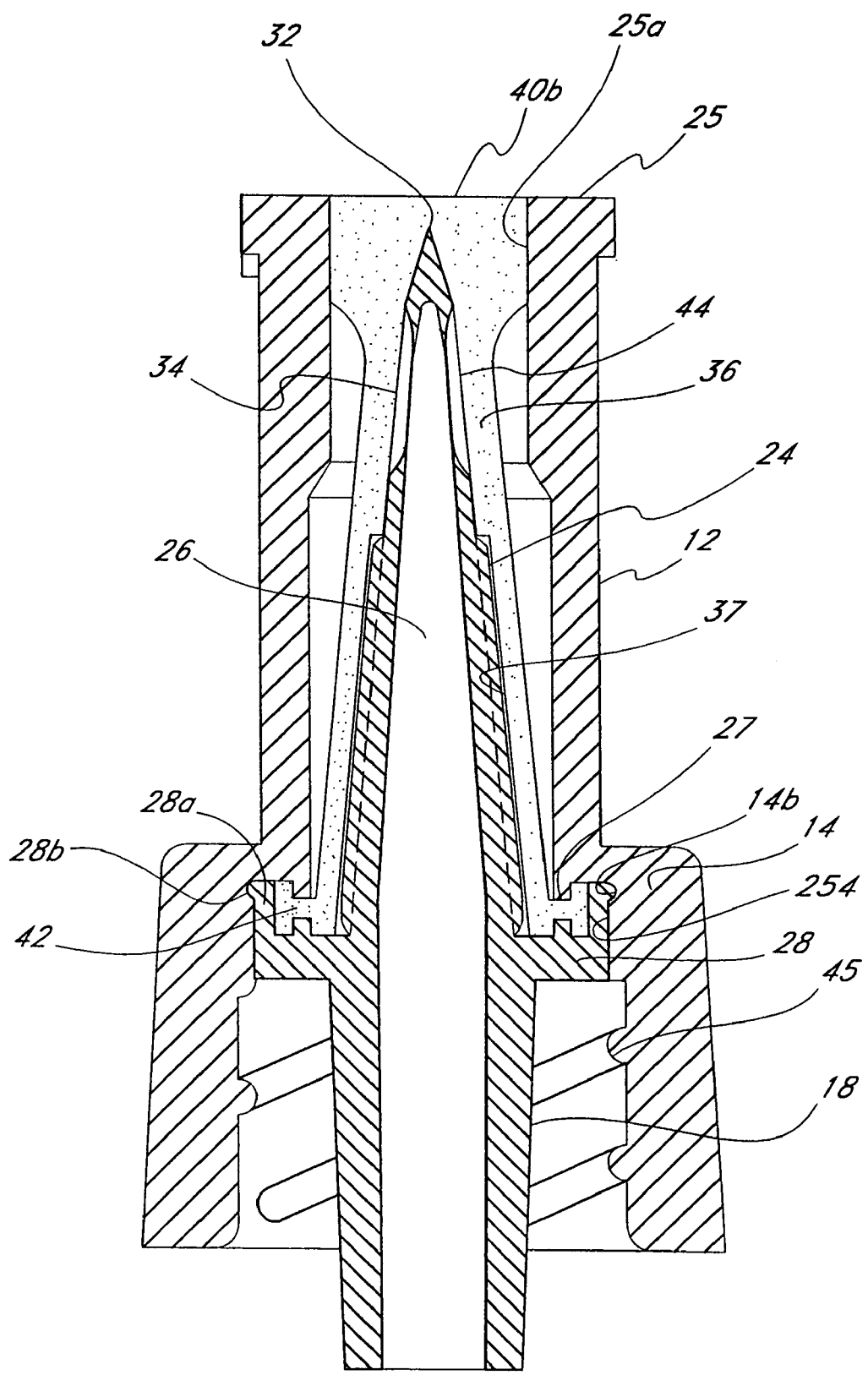
FIG. 3 is a longitudinal cross-sectional view of the assembled valve of FIG. 1.
Figure 4:
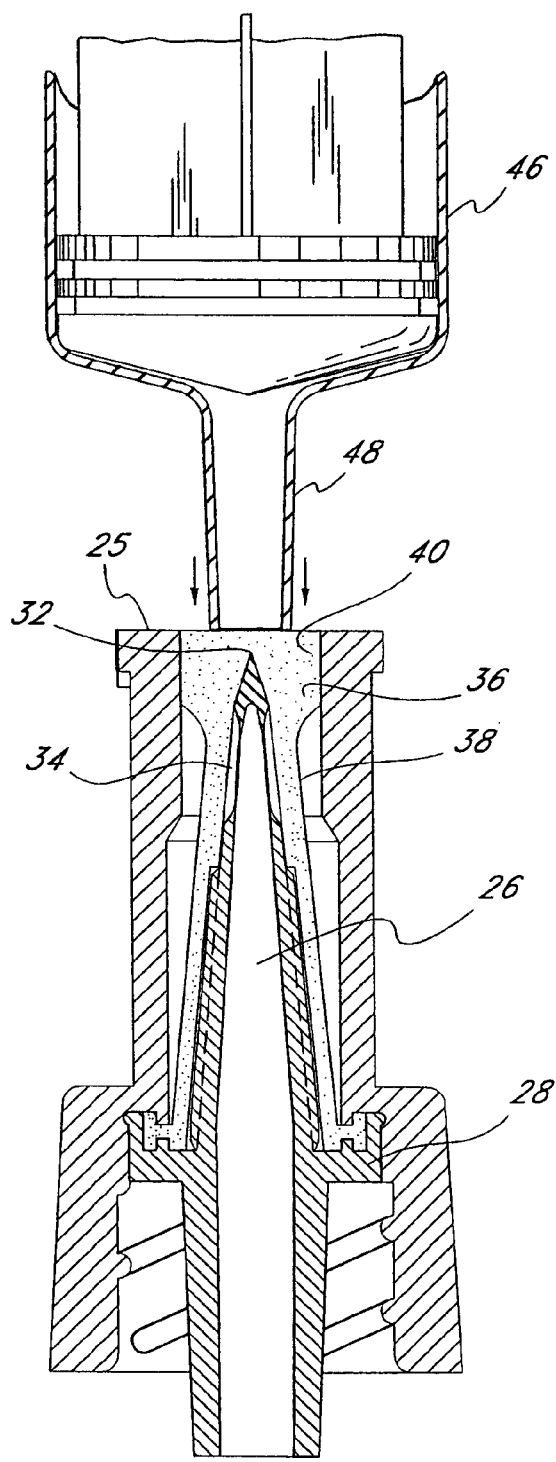
FIG. 4 is a schematic, longitudinal, cross-sectional view of the assembled valve of FIG. 1 before compressing that seal.
Figure 5:
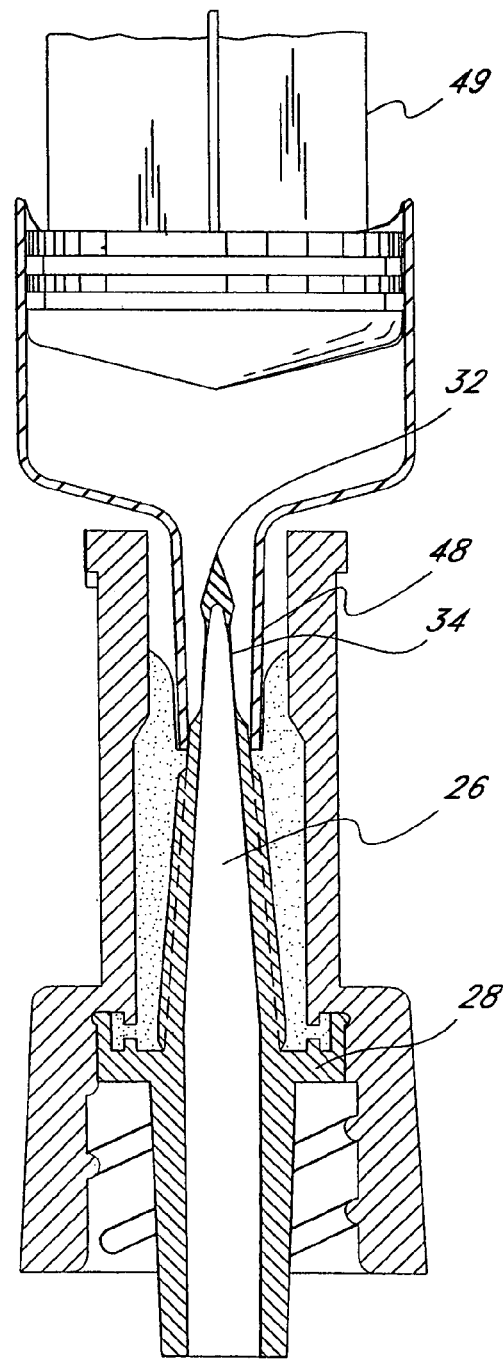
FIG. 5 is a schematic, longitudinal, cross-sectional view similar to FIG. 4 showing the valve during compression of the seal.
Figure 13:
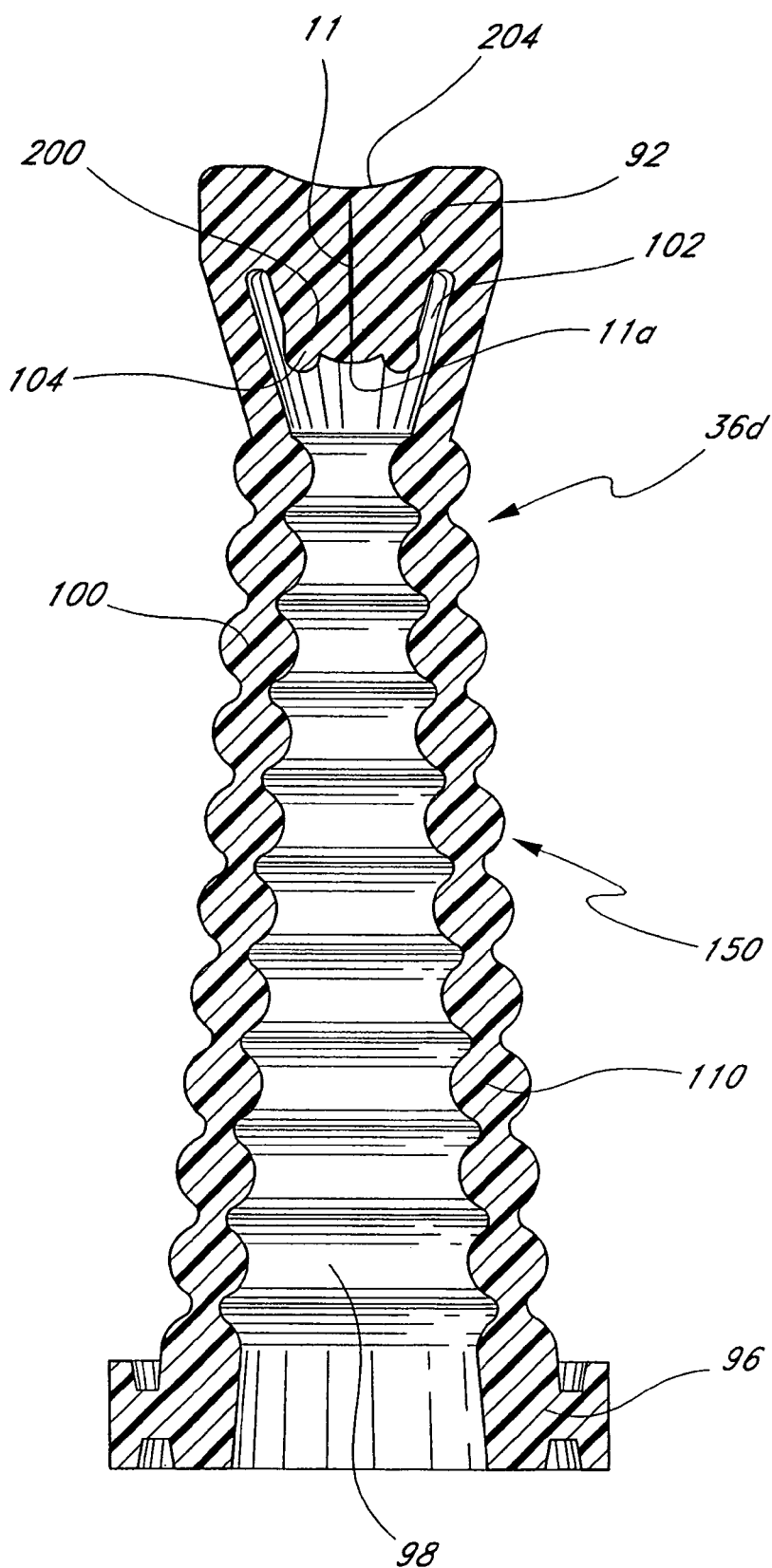
FIG. 13 is a longitudinal cross-sectional view of the sixth embodiment of the seal.

As best shown in FIGS. 1 and 2, the first embodiment of the invention, valve 10, includes a valve body or housing 12, a spike element 24, and a seal 36. The seal 36 is prepared from a resilient material that is flexible, inert, impermeable to fluid, and readily pierceable by the spike 26. In the embodiment shown in FIG. 13 depicting an alternate shaped seal 36d, this seal 36d has a precut slit 11 in its proximal end. This provides a tiny orifice through which the tip 32 of the spike element 24 may easily pass, yet still provides a fluid tight seal upon withdrawal of the spike element. These three components are assembled, as depicted in FIG. 3, with the spike element 24 enclosed to prevent accidental sticks. FIG. 2 illustrates how the housing 12, seal 36, and spike element 24 are attached without the need to use any adhesive or other bonding agent or process. Mechanical connection which provides a fluid tight closure is attained as is discussed subsequently. As shown in FIGS. 4 and 5, the seal 36 moves within the housing 12, being pierced by the spike element 24 to expose the tip 32 of the spike element 24 to allow fluid to flow through the valve 10.

Referring to FIG. 1, one preferred embodiment of housing 12 has a bell-shaped skirt 16 and an upper, preferably cylindrical, conduit 20. The skirt 16 is integral with, and connected by an annular ring 14, to the upper conduit 20. The skirt 16 creates a shield for an inner conduit 18 of the spike element 24. This inner conduit 18 is preferably cylindrical in shape, and slightly tapered. Inner conduit 18 and upper conduit 20 comprise aligned hollow tubes so that inner conduit 18 and upper conduit 20 are in fluid communication with one another when the spike element 24 pierces the seal 36. there is an annual lip 25 surrounding a circular opening 25a in the top of the conduit 20 (see FIG. 2).

In the first embodiment, the upper conduit 20 is adapted to receive the tip or nose 48 of an ANSI standard syringe 46 (see FIGS. 4 and 5). It is, however, contemplated that the outer diameter of the upper conduit 20 can be of any size to accommodate the attachment of other connector devices thereto. Advantageously, the proximal end of the upper conduit 20 can be equipped with a locking mechanism to facilitate locking of the valve 10 to a variety of connector devices. For example, referring to FIG. 1, locking ears 22 near the proximal lip 25 of housing 12 are preferably provided such that the housing 12 can be locked into any compatible Luer-Lock device known to those with skill in the art. For example, referring the FIG. 19, conventional Luer-Lock threads 180 can be provided on the outer diameter of upper conduit 20.

Referring to FIG. 2, the spike element 24 has at its distal end the inner conduit 18 and its proximal end a hollow spike 26 which is integral with the inner conduit. The inner conduit 18 and spike 26 present a continuous passageway for fluid during use. An annular cuff 28 on an intermediate portion of the spike element 24 is integral with, and interconnects, the inner conduit 18 and the spike 26. As illustrated in FIG. 3, the rim 28a of the cuff 28 abuts the underside of the inner ring 14, and has an annular detent 28b that snaps into an annular groove 14b in the underside of the ring. The cuff 28 services two functions. First, it serves as an attachment device to the underside of the annular ring 14. Second, it serves as a support and attachment device for the seal 36.

The hollow spike 26 has a tapered conical shape, ending in a sharp, pointed tip 32. Preferably, along the length of the spike are raised, protruding ridges 30. These raised ridges 30 extend from the surface of the spike preferably between 0.2-2.0 mm. The ridges 30 are preferably aligned along the length of the spike as illustrated in FIG. 2. These ridges 30 serve to break any vacuum created when the spike 26 is sealed as described hereinbelow. Modifications to the alignment and orientation of the ridges are discussed hereinbelow in association with their function. Just distal the spike tip 32, there is situated at least one longitudinal through-hole 34 to permit fluid communication between the inner conduit 18 and the upper conduit 20. Preferably, there are three through-holes 34 within about 0.200 inch from the spike tip 32. These through-holes 34 may be of any size, however, the larger the size of the through-holes the greater the fluid flow rate through the valve 10. In a preferred embodiment, the size of the through-holes 34 are 18-gauge to provide a flow rate three times that of a standard 18 gauge needle.

The seal 36 has a seal cap 40 with a generally flat top surface 40b, an outwardly tapered sidewall 38, and a lower lip 42. Its interior is hollow to provide the conically shaped cavity 37 (FIG. 3). Thus, the seal 36 slips easily over the spike element 24 to fit snugly within the cavity 37. The seal lip 42 is seated within the annular cuff 28 and wedged between the cuff and the underside of the ring 14. There are longitudinal grooves 43 (FIG. 2) along the length of the seal 36 which provide air pockets that facilitate compression of the seal 36 during use. The grooves 43 may be of variable shape or size to facilitate seal compression. In the first embodiment, there is a single groove 43 which completely surrounds the seal 36 between the seal cap 40 and the lip 42.

The base of the seal 36 has a width such that the seal lip 42 fits snugly into the annular cuff 28. The hollow interior or cavity 37 (FIG. 3) of the seal 36 is preferably tapered to conform internally to the shape of the spike 24, having a wall portion 44 which contacts the spike 24 distal seal cap 40. The exterior of the seal 36 is sized and shaped to fit inside the upper conduit 20 of the housing 12. The cap 40 reseals the valve 10 when the top surface 40b is above the through-holes 34. Preferably, the cap 40 substantially fills the opening 25a in the top of the conduit 20. Thus, after assembly, the top surface 40b of the seal cap 40 is essentially flush with the lip 25, so that the lip 25 and seal cap 40 can be swabbed with alcohol or other disinfectant without leakage of disinfectant into the valve 10. It is important that the surface 40b be exposed so that it may be swabbed with a disinfectant.

As best shown in FIG. 3, the spike 24, with contiguous inner conduit 18, is affixed to the housing 12 through the association of the external portion of annular cuff 28 and the internal portion of annular ring 14. Although not necessarily required, these two pieces may be affixed by any one of a variety of methods known to those of skill in the art including, but not limited to, heat sealing, glue, pressure lock, bonding or the like. The seal 36 fits into the annular cuff 28 and is held in place by an internal lip 27 along the internal portion of the annular ring 14 of the housing 12. The length of the spike 24 is such that, after assembly, the tip of the spike rests below the plane defined by the lip 25 of the housing 12. Preferably, the spike tip 32 is approximately from 0.525" to 0.1" below the lip 25 of the housing 12. The seal 36 fits snugly against the spike 24 and is essentially flush with the lip 25 of the housing 12. The spike tip 32 is thus embedded within the seal cap 40 prior to use or may be approximately 0.025" distal the seal cap 40 when the valve 10 is in the closed position. The inner conduit 18 is partially shielded by the bell shaped skirt 16 of the housing 12 (see FIGS. 1-3). The inner surface of the bell shaped skirt 16 preferably has protruding threads 45 as an optional locking mechanism for attaching a medical implement thereto. Further, other medical devices can be pressure fit over the outer portion of inner conduit 18 without direct association with the protruding threads 45.

During use, the invention is designed to adapted as a two-way valve. The orientation of the valve is independent to fluid flow and dependent on the preferred orientation of the preexisting connections. Thus, the invention can be used as a valve connector for an intravenous central or peripheral piggyback connector in either orientation. Parenteral fluid is delivered to patients through tubing such that the liquid flows from a container through a needle into the patient. The containers are frequently changed or additional fluid bottles are added. The invention disclosed herein is designed to interconnect medical implements along the route of fluid delivery to the patient. However, the invention is also useful in any environment in which a resealable fluid valve is desired. During use, a connector of the appropriate size is fitted over the inner conduit 18. Locking can be achieved by a Luer-Lock mechanism, a pressure fit or any other locking mechanisms know to those with skill in the art, as described above. Thus, in one example, fluid passes from the inner conduit 18 into the spike 26. However, fluid flow is locked in place by the seal 36.

FIGS. 4 and 5 illustrate valve activation. In FIG. 4, the medical implement connecting to the proximal end of the valve 10 is a syringe 46. However, this connecting implement could be any number of medial implements known to those of skill in the art. The nose 48 of the syringe 46 is placed on the seal cap 40 inside the lip 25 of the housing 12. The application of pressure on the syringe 46 in the direction of the arrows, as illustrated in FIG. 4 creates pressure on seal cap 40. The resulting downward pressure compresses the seal 36. This pushes the tip 32 of the spike 26 through the seal cap 40 to expose the through-holes 34. Compression is facilitated by the grooves 38. Fluid is now able to flow into the syringe 46, or vice versa, depending on whether fluid is to be withdrawn from the patient or medication injected into the patient. FIG. 5 shows valve 10 opened by insertion of the nose 48 of the syringe 46 into the opening 25a. A syringe plunger 49 in the syringe 46 is retracted thereby creating a vacuum to draw fluid through the valve 10 into the syringe. For intravenous applications, the valve 10 can be orientated in the position diagramed in FIGS. 4 and 5, or it can be rotated 180° such that fluid flows in the opposite direction.

Upon removal of the syringe from spike 26, as shown in FIG. 4, the seal 36 is free to return to its original shape and over through-holes 34. The ability of the seal 36 to return to its original shape is determined by the resiliency of the material used to prepare the seal 36. In addition, the ability of the seal 36 to return to its original shape is facilitated by the protruding ridges 30 formed on the external surface of the spike. During compression, a vacuum may form in the area between the spike 26 and the seal 36, thereby preventing the seal 36 from returning to its original position. The protruding ridges permit air to pass along the spike/seal interface to prevent vacuum formation and allow free return of the seal. The ability of the seal 36 to deform reversibly and return to its original position is particularly useful because (1) it immediately stops fluid flow through the valve 10, (2) it covers the recessed spike 26 to maintain its sterility, and (3) it reduces the risk that the spike could inadvertently pierce another object or person. In addition, since the valve 10 lacks movable parts, except for the seal, it is unlikely that when the seal 36 is pushed down, the valve 10 would fail to function.

Advantageously, the through-holes 34 are located relatively low on the spike 26. Thus, the through-holes 34 are seated relatively early in the process as the seal 36 returns to its original configuration with the valve 10 is closed. In one preferred embodiment the through-holes 34 are located 0.075" below the spike tip 32 (see FIG. 2). Additionally, the through-holes 34 are sealed if the seal 36 does not fully return to its original configuration depicted in FIG. 4. Further, the ability of the seal 36 to return reversibly to its original position permits the reuse of the connector valve 10. Following disconnection, and before reuse, the surface of pierced seal cap 40 is essentially flush with the housing 12. Thus, this flush surface can, advantageously, be sterilized with alcohol or other surface decontaminating substances. The skirt 16 and upper conduit 20 advantageously shield both connections from the surrounding environment to protect the sterility of the connection. Further, both the skirt 16 and upper conduit 20 function as collection reservoirs to prevent fluid from dripping from the valve 10 during manipulation.

A cover cap (not shown) can be supplied to fit over the upper conduit 20 as further protection for the seal surface between use. Such a cover cap, however, is not needed to maintain sterility since the seal 36 may be swabbed with a disinfectant after each use. The reversibility of the seal 36 makes the valve 10 particularly attractive as a connector valve to provide fluid communication between two fluid lines. Therefore, the present invention provides for placing a first fluid line in communication with a second fluid line using the valve disclosed herein. The reversibility of the valve 10 permits multiple fluid lines to be successively added, for example, to a fluid line in direct communication with a patient's vein. Since the valve is easily sterilizable and sealable, fluid lines can be added and removed without disconnecting venous contact.

The valve 10 is preferably prepared from a hard plastic, but it is additionally contemplated that the valve could be prepared from other medically inert materials known to those in the art. the spike element 24 is preferably prepared from the same material as the housing 12. One particular advantage of this invention is that it does not rely on the use of metal needles. This dramatically reduces the risk of skin puncture during use and manufacture. Further, the upper conduit 20 serves as a shield to the spike 26 such that skin puncture is further reduced. The spike 26 need only be strong enough to penetrate the seal cap 40, or if necessary, to pierce a connecting septum.

In the embodiment of the invention illustrated in FIGS. 2-4, the through-holes 34 are placed distal spike tip 32. This placement provides two important advantages. First, the placement of the through-holes 34 facilitates resealing of the valve 10 after use. Second, if the through-holes were placed at the spike tip 32, the holes 34 may core the seal cap 40 thereby introducing seal particulate into the fluid flow and possibly plugging the holes 34. Thus, the longitudinal placement of the through-holes distal spike tip 32 prevents the introduction of particulates into the fluid path and/or plugging of the through-holes 34. It is additionally contemplated that the number and diameter of the through-holes 34 can be adjusted to accommodate different fluid velocities. In a preferred embodiment, the preferred velocity of fluid passing through the through-holes 34 is equal to or greater than the flow rate through an 18 gauge needle. Through-holes larger than 18 gauge will, of course, facilitate greater fluid velocities.

An important advantage of the invention is that the valve 10 has very little dead space, thus the volume of liquid entering into the valve is substantially equivalent to the volume of fluid leaving the valve. Further, the total equivalent fluid volume of the valve is very small such that the volume of fluid flowing through the system in order to place the valve in fluid communication with a medical implement such as a syringe 46 is substantially zero.

Alternate Embodiments

In another preferred embodiment of the invention, illustrated by FIGS. 6 and 7, a disposable sterile adaptor valve 50 is provided to function as a resealable lid for a container (not shown) of fluid. The fluid can thus be removed from the fluid container or permitted to flow from the container into a medical implement adapted to house fluid in a sterile manner. As is the conventional practice, an open mouth of the container will ordinarily be sealed with a cover member (not shown).

FIG. 6 shows an adaptor valve 50 having a body including an adaptor skirt 52. The adaptor skirt 52 will preferably fit snugly over the open mouth of the container. The skirt 52 may be of any size to accommodate a range of container sizes. A lengthwise slit 54 is preferably provided in at least one location along the length of the skirt to ensure a snug fit between the skirt 52 and the container. A chamber 56, preferably tubular in configuration, extends upward from the skirt 52 and is similar in construction and design to the upper chamber 20 of the first preferred embodiment. Similar to the first embodiment, the proximal portion of the valve contains a locking mechanism 59 that preferably comprises a Luer-Lock device or other locking device known to those of skill in the art.

As depicted in FIG. 7 a spike 58 extends upward through a tubular chamber 56. A spike tip 60 is preferably recessed from a proximal lip 62 of the tubular chamber 56. In a closed position, this tip 60 is covered by a seal 64, which is essentially the same as seal 36. Protruding ridges 66 and seal grooves 68 facilitate seal compression in the open position and promote closure following use. Thus, in the closed position as illustrated in FIG. 7, the seal 64 covers the through-holes 70 to prevent fluid out-flow from the container. The adaptor valve 50 contains a second spike 72 which points in the opposite direction as spike 58. These spikes 52 and 72 are in fluid communication with each other. The spike 72 extends downward inside the adaptor skirt 52. The two spikes preferably form one component of the valve 50 while the skirt 52 and upper chamber form a second component. These two components can be assembled in a manner like that of the valve 10. The spike 72, like the spike 58, has longitudinal through-holes 74 and a tip 76. The through-holes 74 are located inward of the tip 76. The adaptor valve 50 is thus useable with containers holding sterile medicament having a cover or septum seal at the open mouth of the container. Examples of containers with such seals contemplated for use with this invention include dosage bottles for intramuscular injector antibiotic containers or the like. However, it is also contemplated that the valve 50 can be adapted with its own seal and locking mechanism to permit the valve to be employed on a variety of containers for medicaments or other fluids. Medicaments in these types of containers are preferably maintained under sterile conditions and the volume and nature of the medicament is such that multiple aliquots are intermittently removed over time. If the medicament is reconstituted, then, during use, any covering over the opening on the container is removed to reveal the rubber septum. The adaptor valve 50 is placed over the septum and direct pressure is applied to pierce distal spike 72 through the septum and into the container. A syringe or the like can then be applied, as depicted in FIG. 4, in association with the first preferred embodiment, to withdraw fluid from the container. The pressure of the nose 48 over the spike 58 pushes spike tip 60 through seal 64. At the same time, seal 64 is pushed back and compresses. Compression is accommodated by seal grooves 68. Fluid is withdrawn from the container and the syringe is removed from the spike 58. Release of the pressure applied to seal 64 permits the seal to return to its original configuration. The spike ridges 66 facilitate seal reversibility.

Often the ingredients housed in containers are those that ca be lyophilized at purchase. Lyophilized ingredients require reconstitution before use. If the medicament requires reconstitution before use, then sterile water, saline, or other fluid can be introduced into the container before fluid is extracted. The two-way nature of the valve permits this without any special adaptation. After the syringe is removed, the adaptor valve 50 automatically seals. Subsequently, aliquots can be removed from the container by syringe or the like. Alcohol or other compatible surface sterilizing agent can be used to wipe the lip 62 and seal 64 before each use. Similar to the first embodiment, it is additionally contemplated that a cap can be provided to fit over upper chamber lip 62 between use.

The adaptor valve 50 can be adapted to function as a medicament adaptor for an intravenous container. In this case, the adaptor valve 50 is placed on a medicament container for intravenous delivery and attached via tubing to an intravenous feed. Thus, the adaptor valve 50 can be placed in fluid communication with a connector valve of FIG. 1 to facilitate the flow of medicament from intravenous drip bottles.

Figure 9:
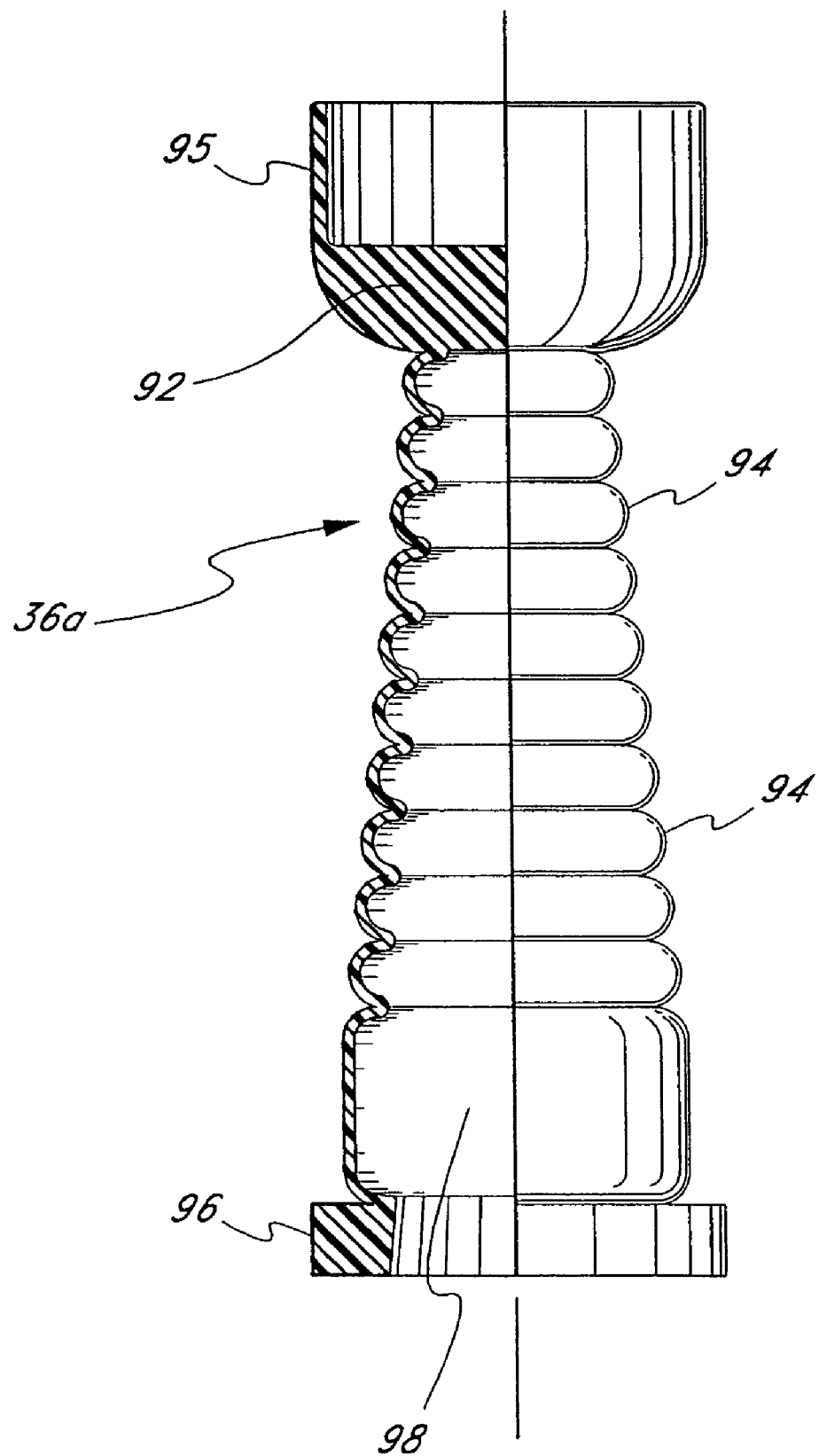
FIG. 9 is a side elevation view, partially in cross-section, of a third embodiment of the seal.

An alternative embodiment of the seal, a seal 36a, is shown in FIG. 9. Seal 36a comprises a seal cap 92 at the proximal end thereof and a seal lip 96 at the distal end thereof. A cup-like annular flange 95 is provided proximal seal cap 92. The seal cap 92 and seal lip 96 are connected by a seal wall consisting of a plurality of ringed wall portions 94 that expand and collapse in an accordion like fashion. During compression of the seal 36a, the diameter of the ringed wall portions 94 expand outward in the radial direction. There are air pockets 13a (FIG. 10) between ring portions 94 and the housing and air pockets 13b between spike 24 and seal 36a. The seal 36a contains a cavity 98 distal seal cap 92 and adjacent the ringed wall portions 94. The seal 36a interacts with spike 26 (FIG. 2) and other components of the present invention in a similar fashion to seal 36 of FIG. 2.

Figure 10:
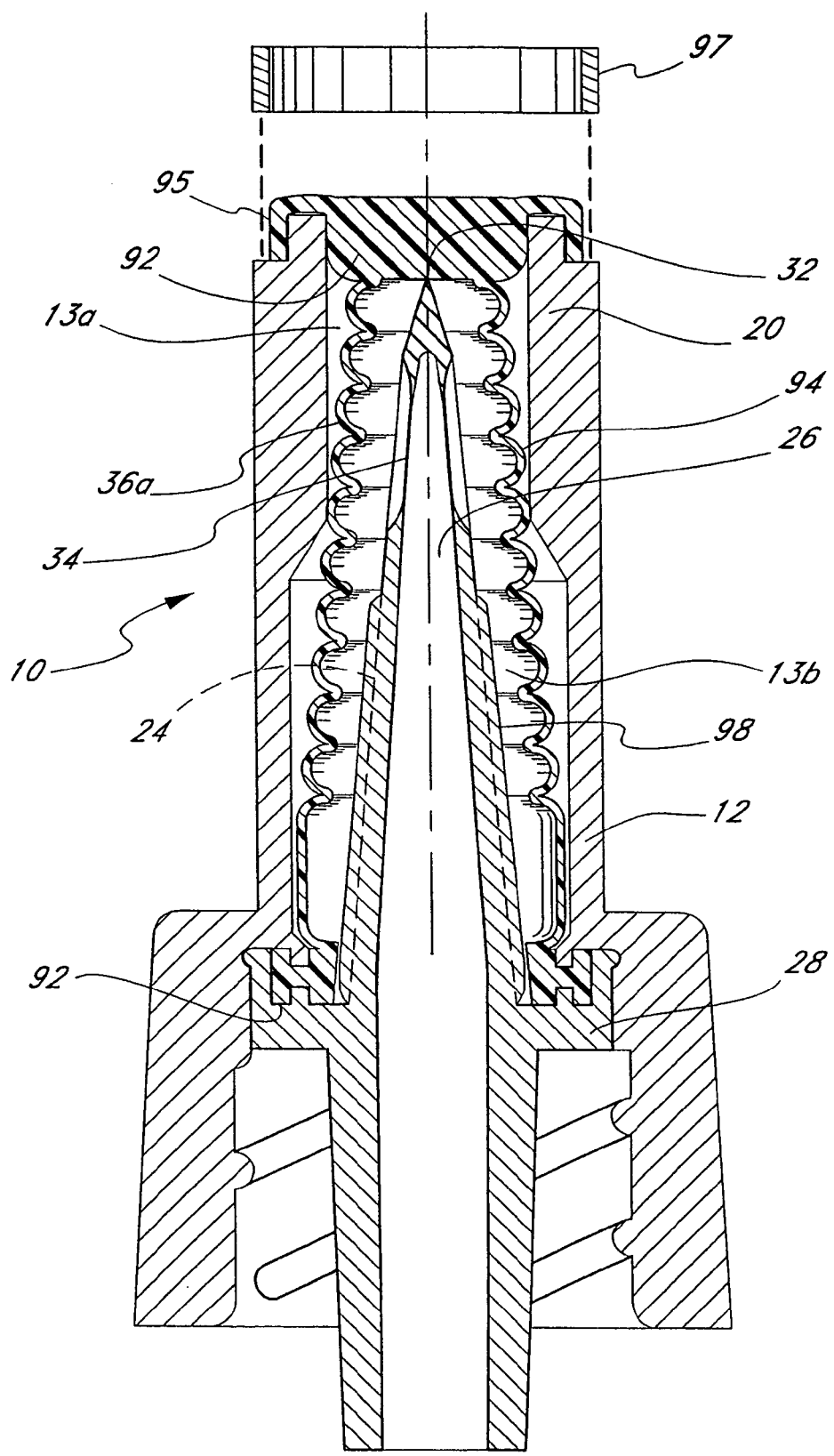
FIG. 10 is a longitudinal cross-sectional view of the assembled valve of FIG. 1 using the seal of FIG. 9.

Referring to FIG. 10, the cup-like annular flange 95 may be stretched around the upper conduit 20 and held in place by an annular ring 97. This creates a trampoline like effect that assists returning the seal 36a to a decompressed state after withdrawal of a syringe (not shown). This embodiment has two advantages. First, the proximal end of the valve 10 can be swabbed with alcohol or other disinfectant without leakage of disinfectant into the valve 10. Second, by affixing cup-like annular flange 95 to upper conduit 20 at the proximal end thereof with annular ring 97, the repeated deformation and reformation of the seal 36a is assisted.

Figure 11:
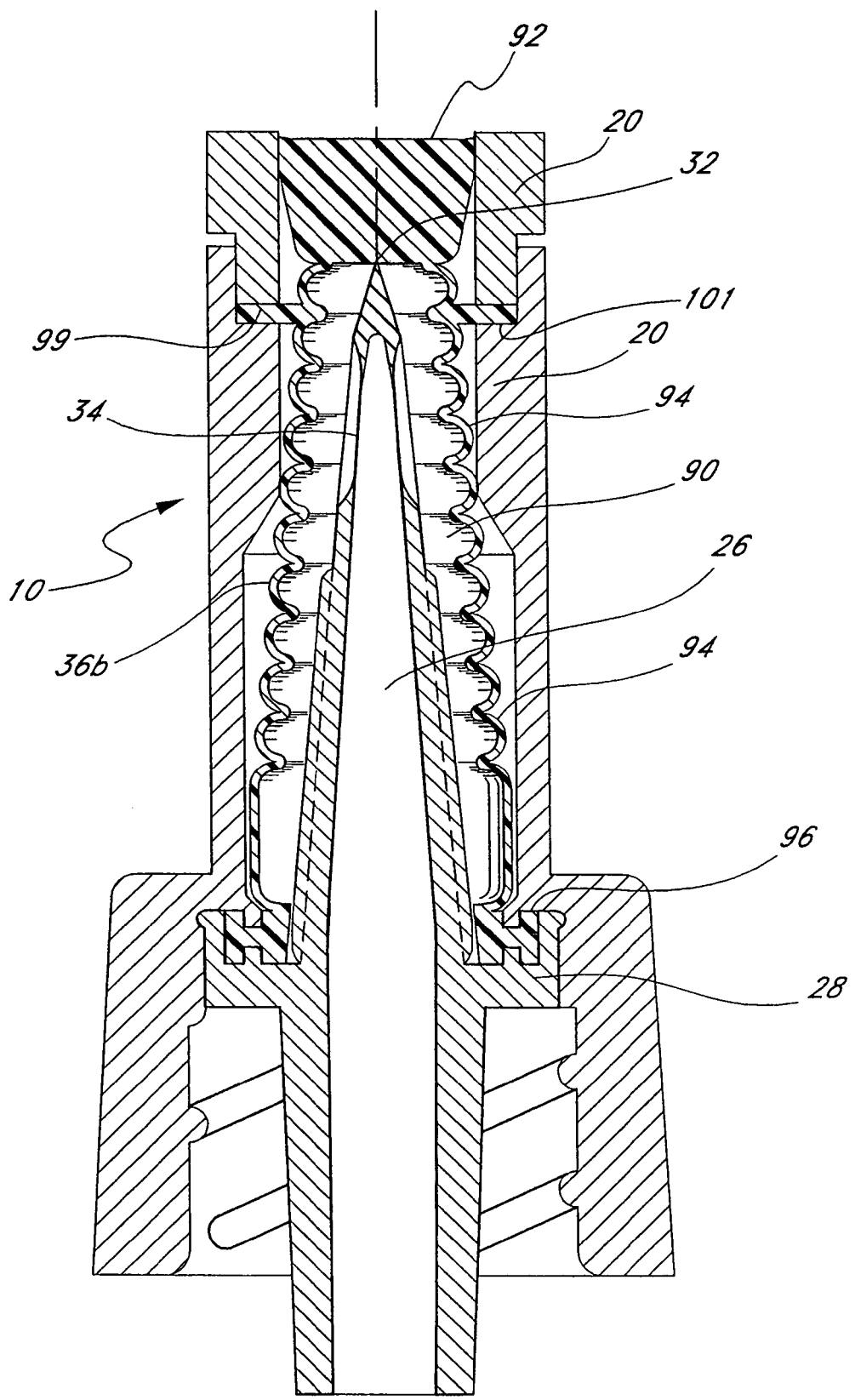
FIG. 11 is a longitudinal cross-sectional view of the assembled valve of FIG. 1 using a fourth embodiment of the seal.

An alternative embodiment of the seal, a seal 36b is shown in connection with the valve 10 in FIG. 11. The seal 36b is similar to the seal 36a and is comprised of seal cap 92, a side wall consisting of ringed wall portions 94 and a seal lip 96. It also has an outwardly extending ring 99 which is at a right angle with respect to the longitudinal axis of the valve 10. This ring 99 is used to attach the seal 36b to upper conduit 20. Preferably, an upper conduit annular plug 20' is inserted within upper conduit 20 to create a tight fit between perpendicular ring 99, a ledge 101 in the upper conduit 20, and the plug 20'. The ring 99 assists in the reformation of seal 36b to enclose spike 26 upon withdrawal of a syringe (not shown).

Figure 12:
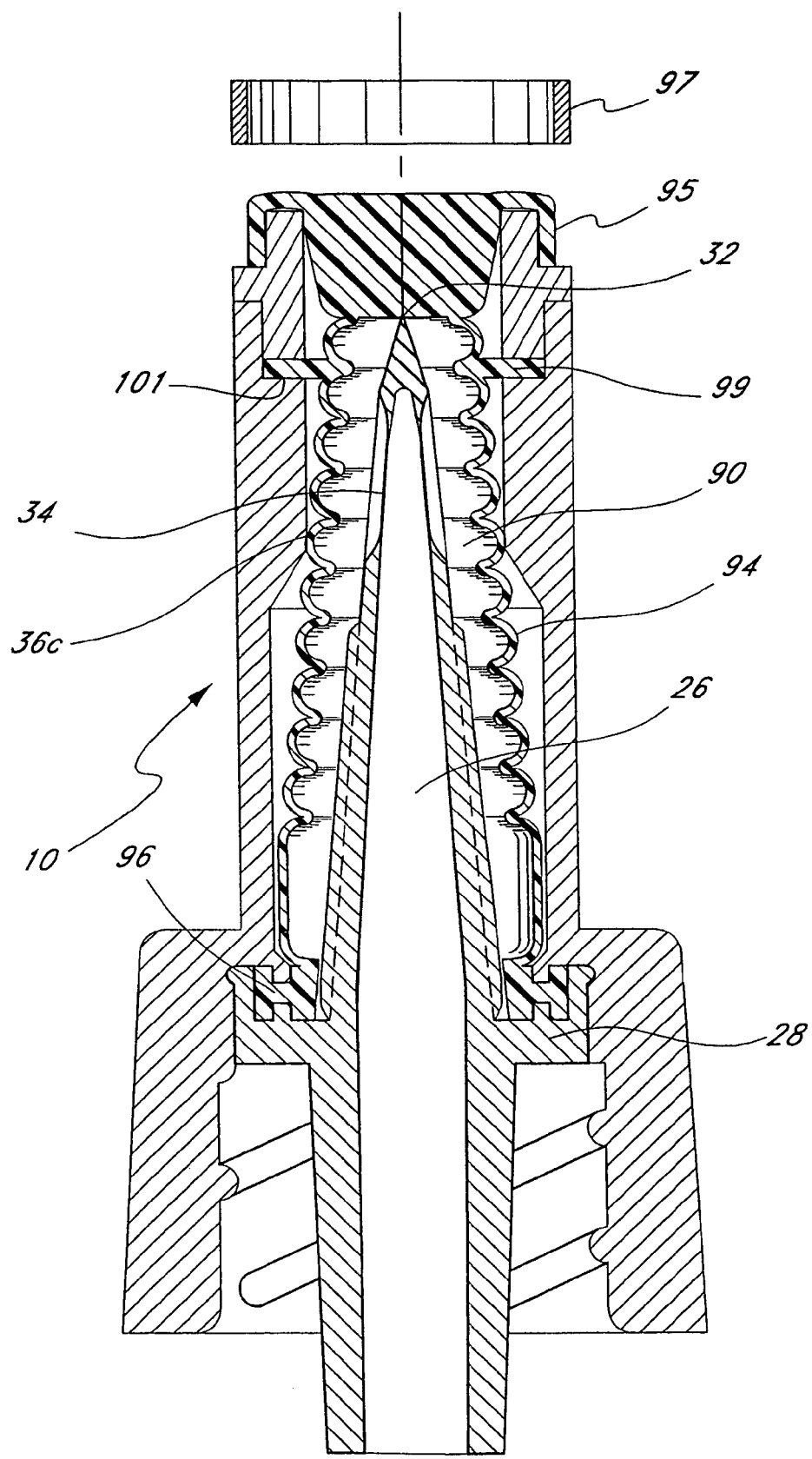
FIG. 12 is a longitudinal cross-sectional view of the assembled valve of FIG. 1 using a fifth embodiment of the seal.

As shown in FIG. 12, the cup-like annular flange 95 and ring 99 may both be used in connection with the valve 10, to provide the seal 36c. This seal 36c, provides rapid reformation upon withdrawal of a syringe (not shown) and realizes the advantages of both the seals 36a and 36b.

Another alternative embodiment of the seal, a seal 36d, is shown in FIG. 13. In this embodiment, the seal 36d is comprised of seal cap 92, seal lip 96, and a side wall 150 comprised of circular tires 100 stacked in series one on top of an adjacent larger diameter lower tire. The circular tires 100 are preferably solid throughout the diameter of the cross-section thereof. These circular tires 100 will deform and reform upon, respectively, compression and decompression of the seal 36d, thereby exposing or covering a spike (not shown) as the case may be.

Figure 14:
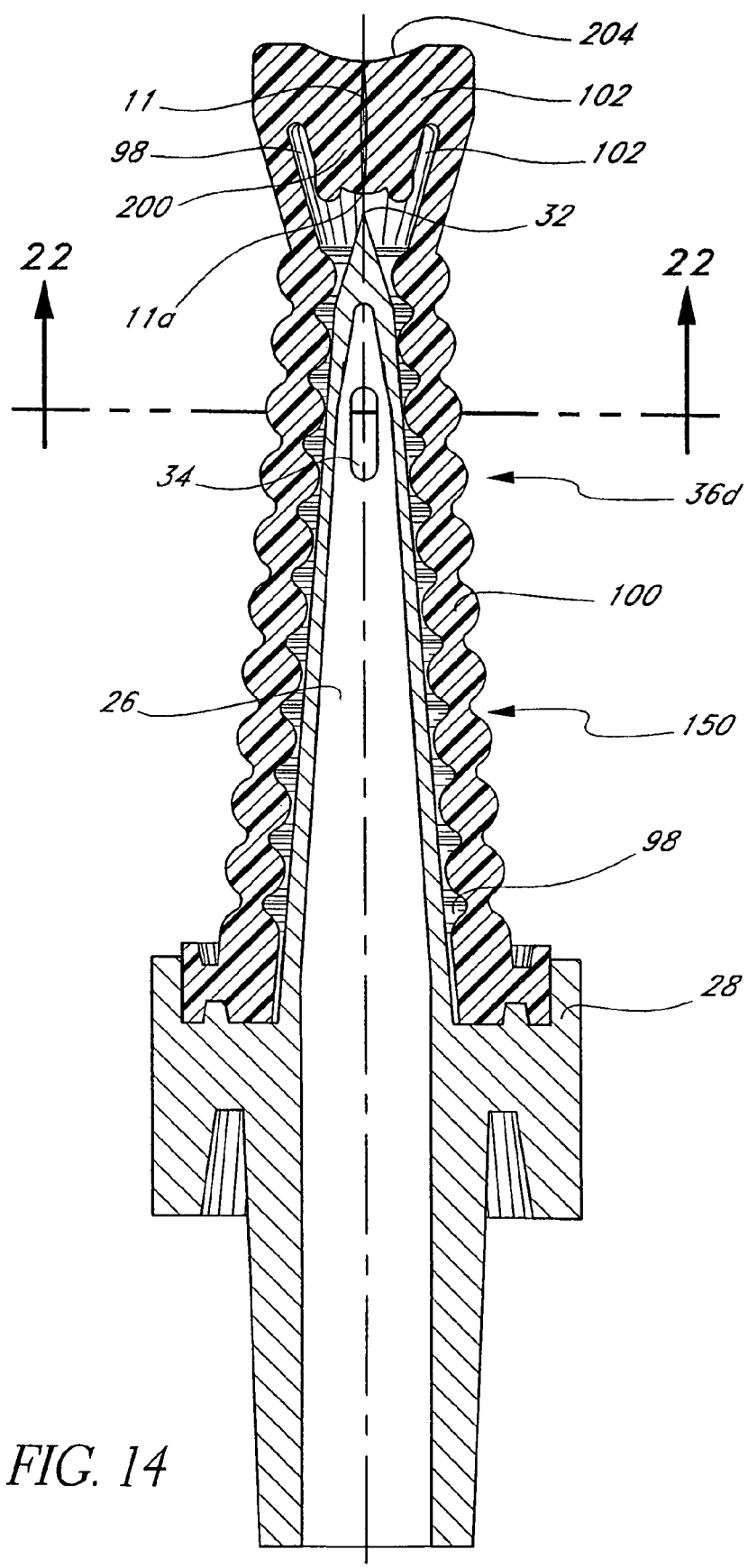
FIG. 14 is a longitudinal section of the seal shown in FIG. 13 used in connection with the spike device shown in FIG. 2.
Figure 15:
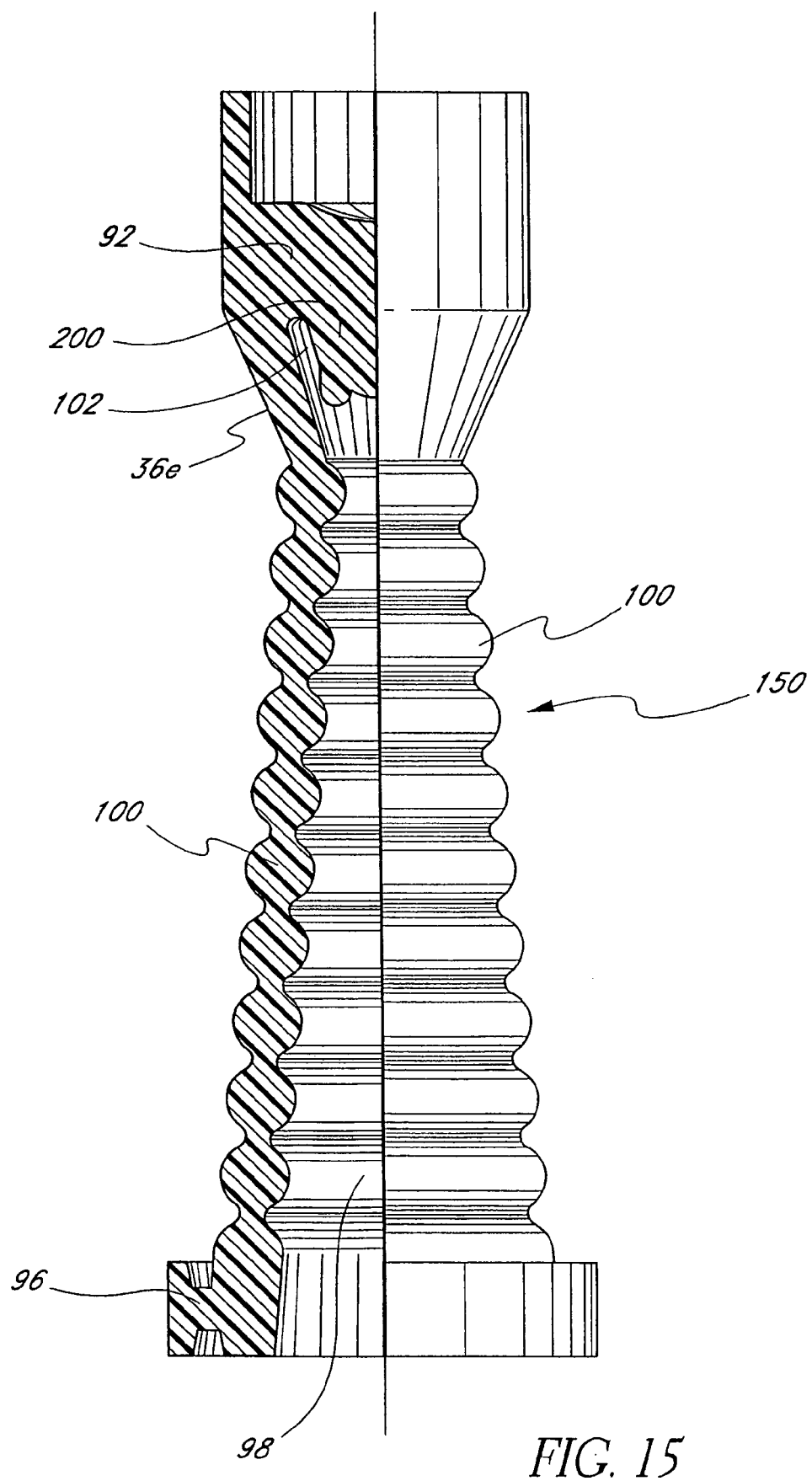
FIG. 15 is a longitudinal partial cross-sectional view of a seventh embodiment of the seal of this invention.
Figure 16:
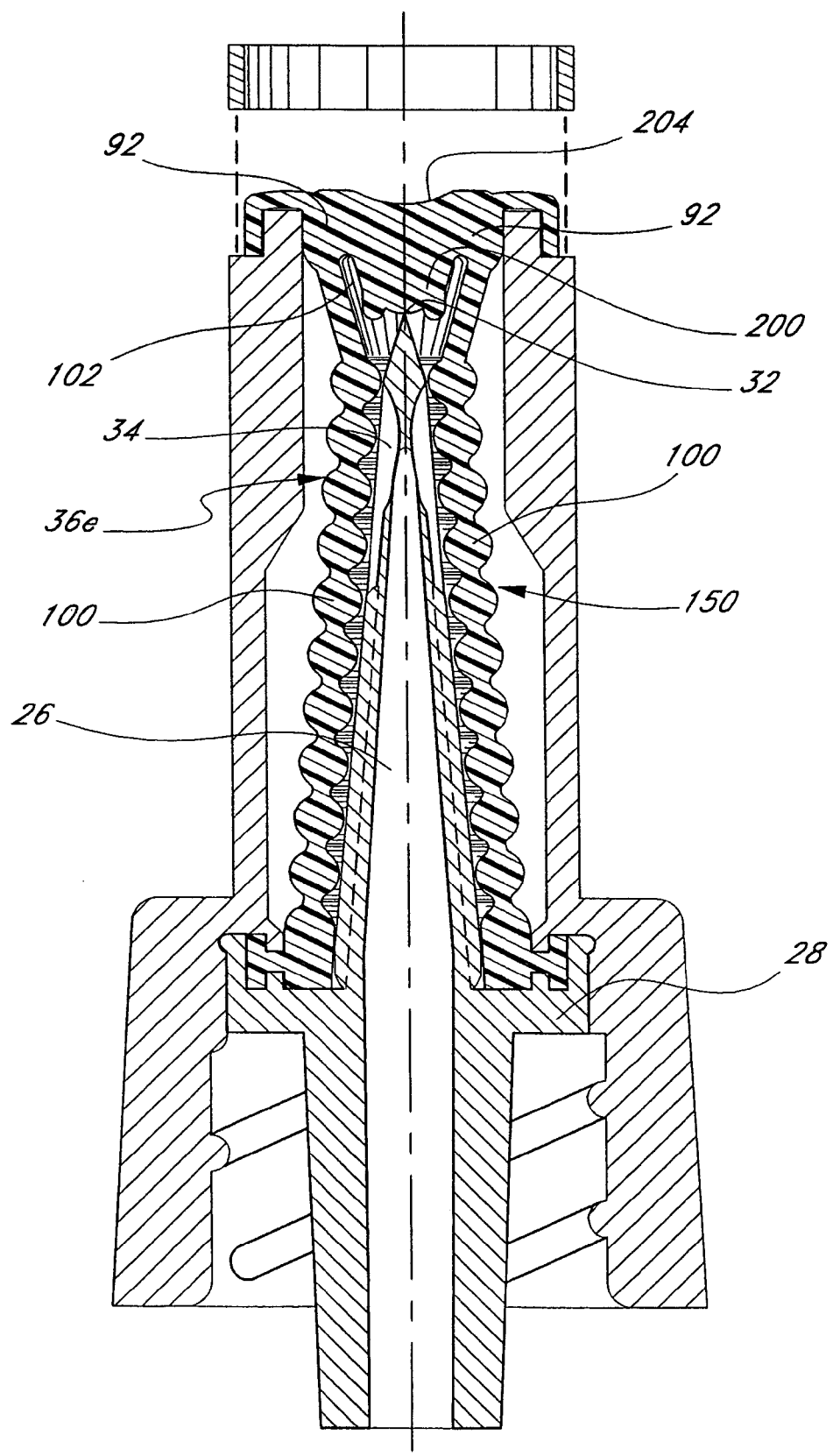
FIG. 16 is a longitudinal cross-sectional view, after assembly, of the embodiment of the valve shown utilizing the seal of FIG. 15.
Figure 17:
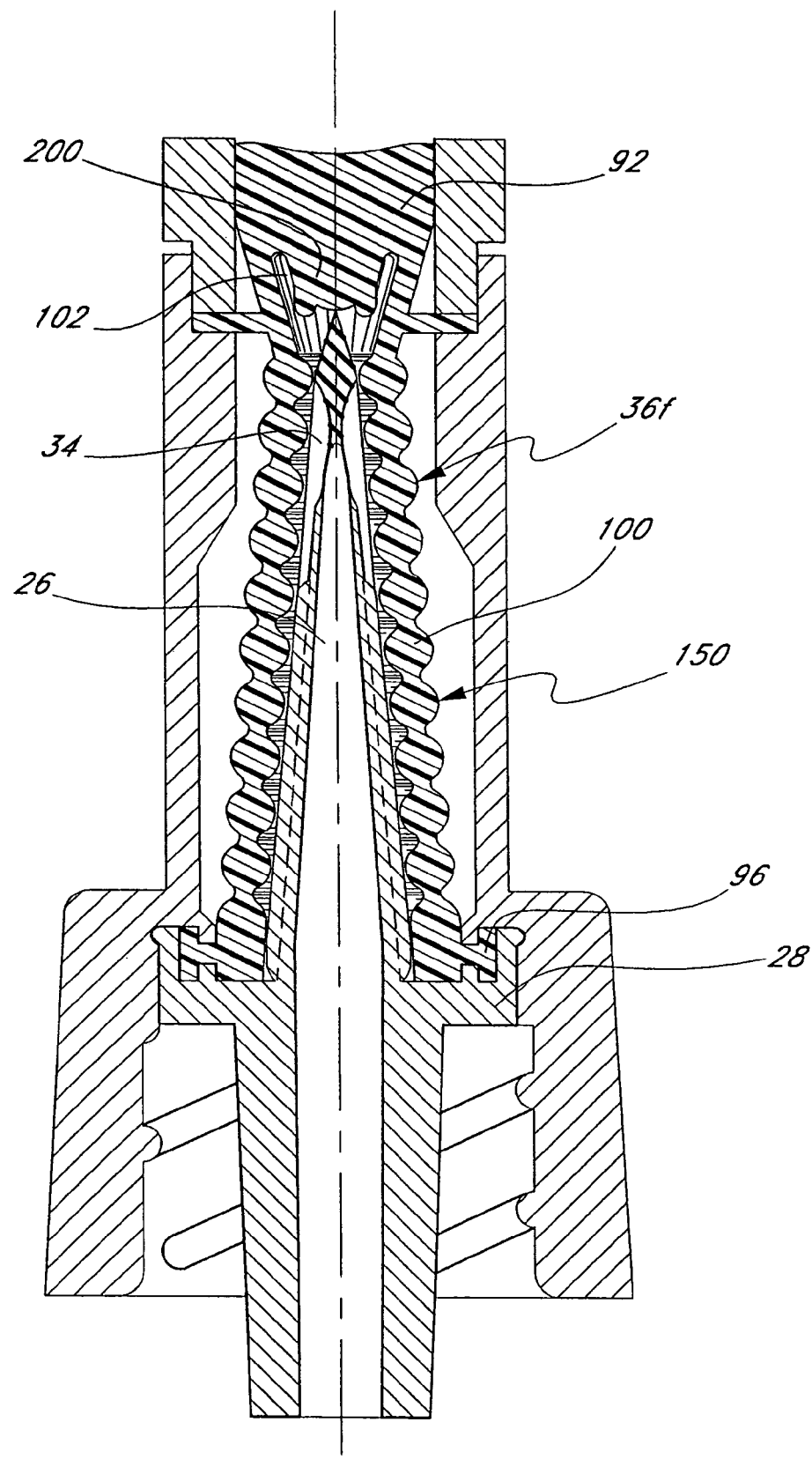
FIG. 17 is a longitudinal cross-sectional view, after assembly, of the eighth embodiment of the valve of this invention.
Figure 18:
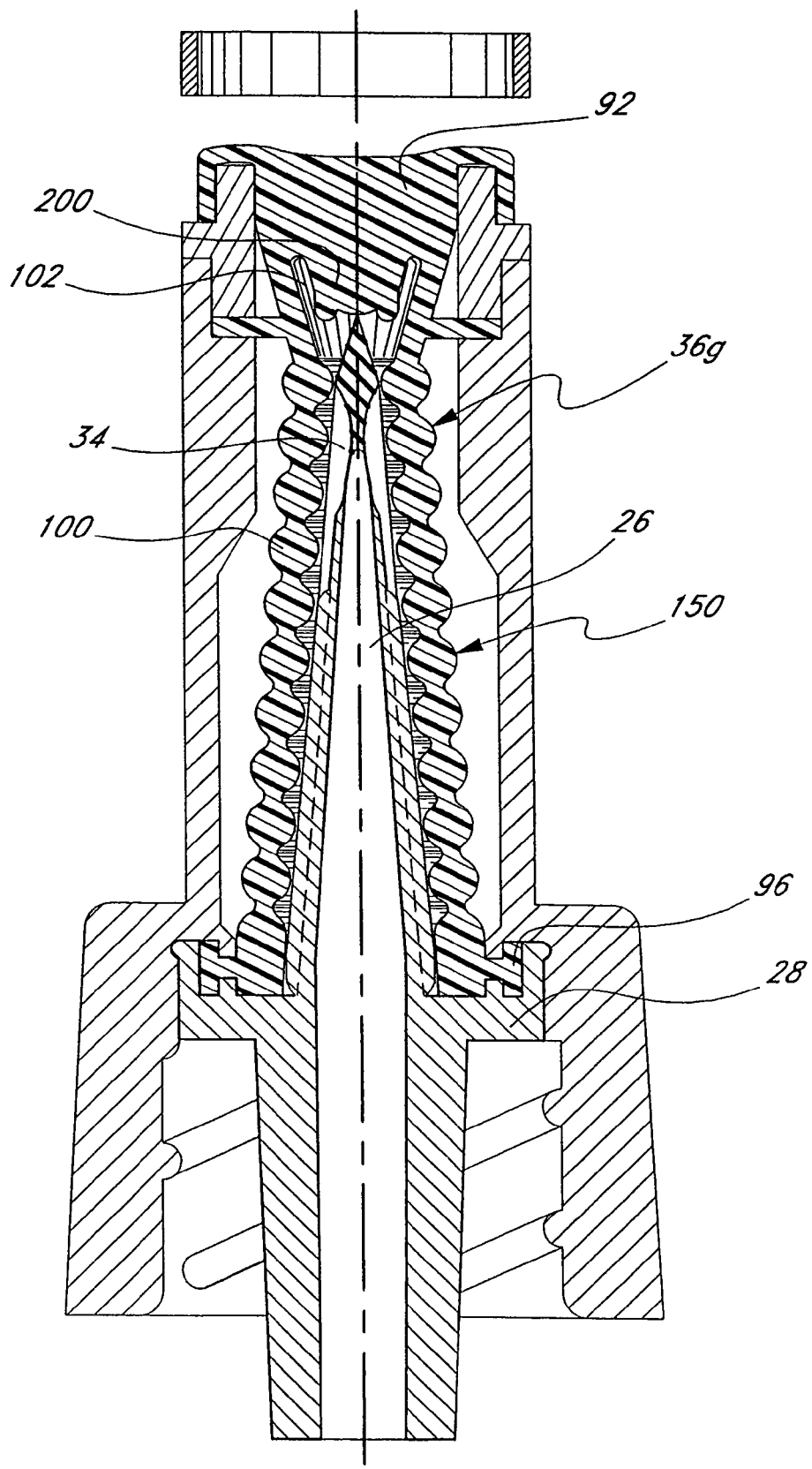
FIG. 18 is a longitudinal cross-sectional view, after assembly, of the ninth embodiment of the valve of this invention.
Figure 19:
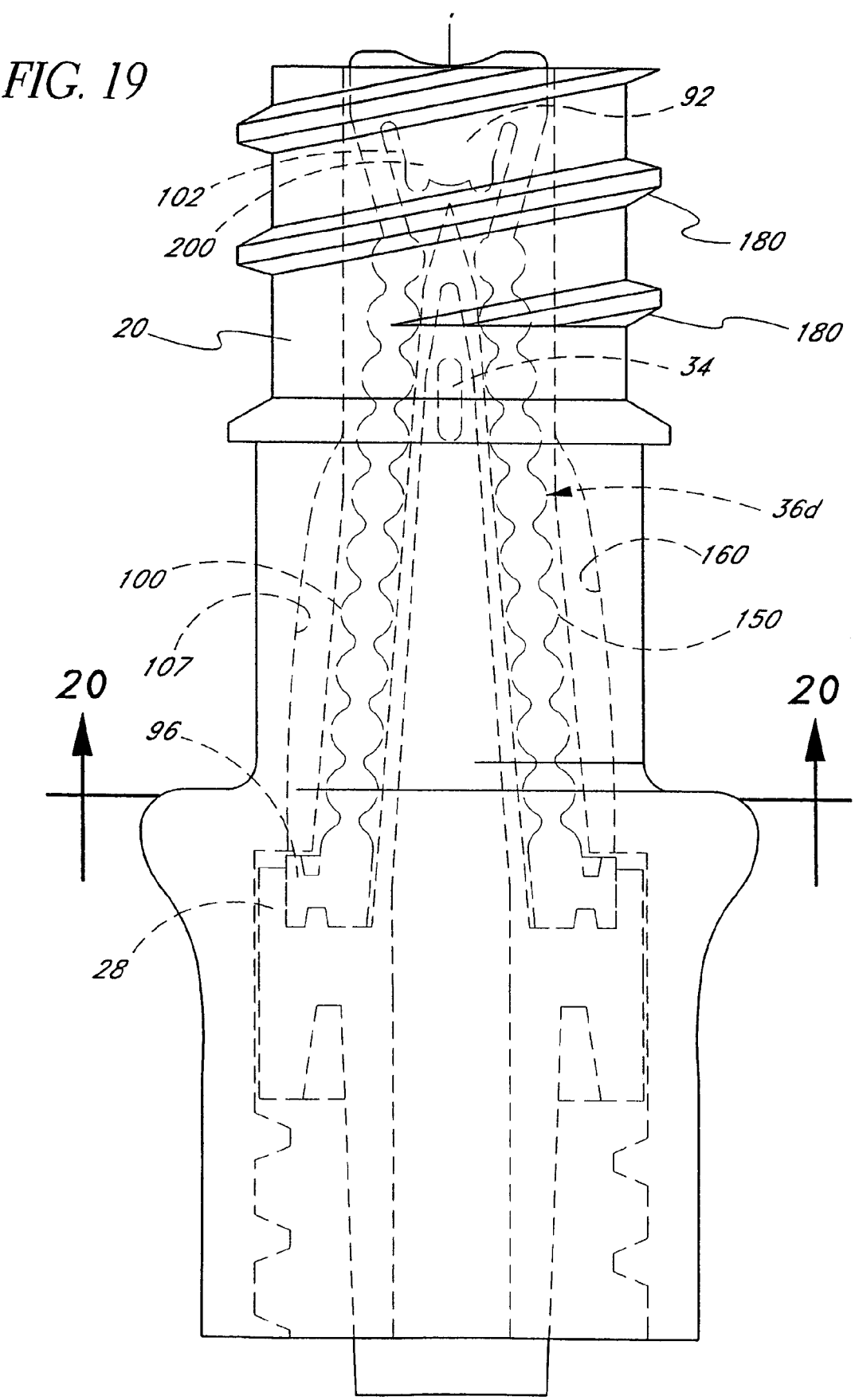
FIG. 19 is a side elevation view, after assembly, of the seal and spike shown in FIG. 14 connected to the body or housing shown in FIGS. 20 and 21.
Figure 20:
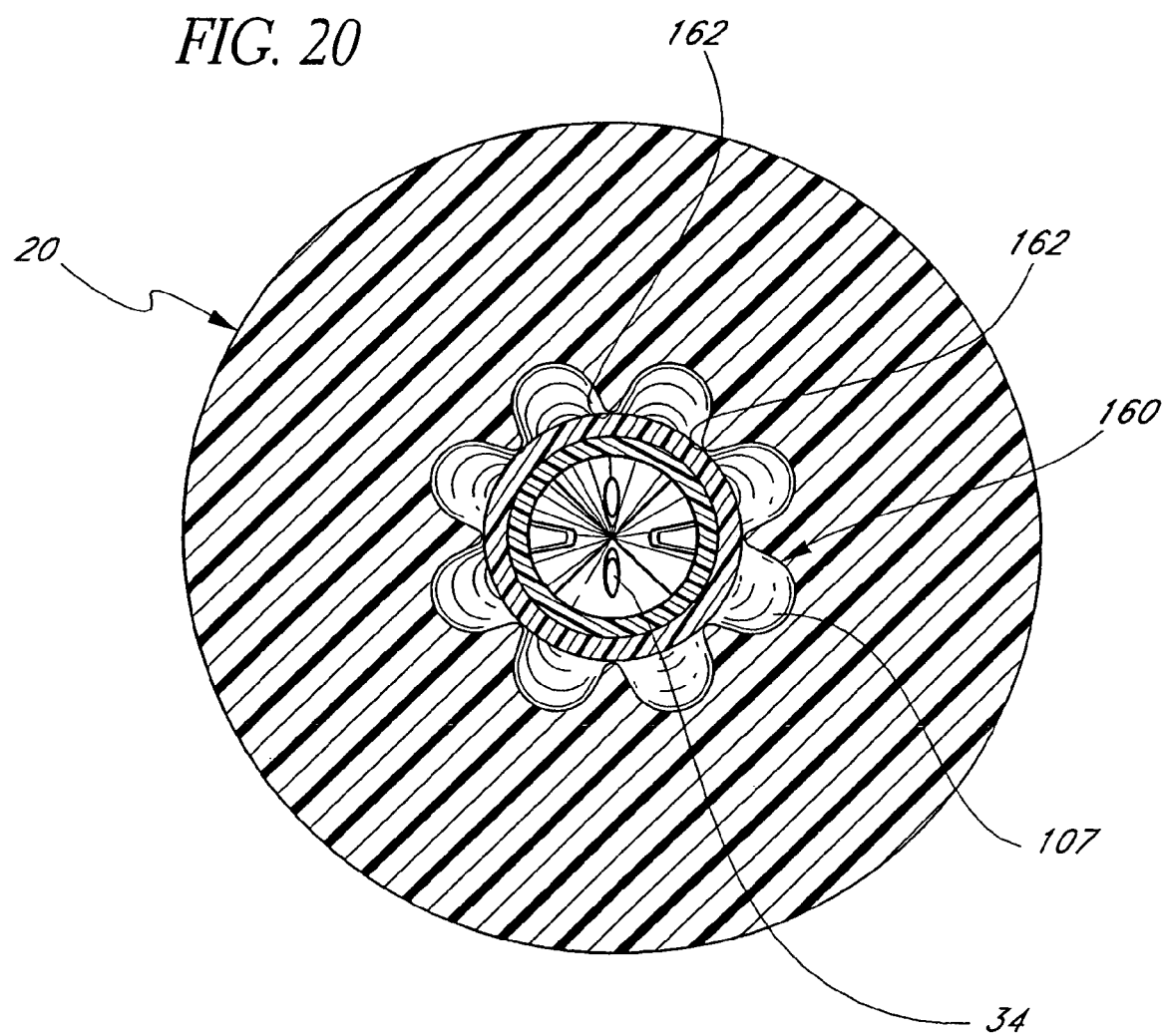
FIG. 20 is a cross-sectional view taken along line 20-20 of FIG. 19.
Figure 21:
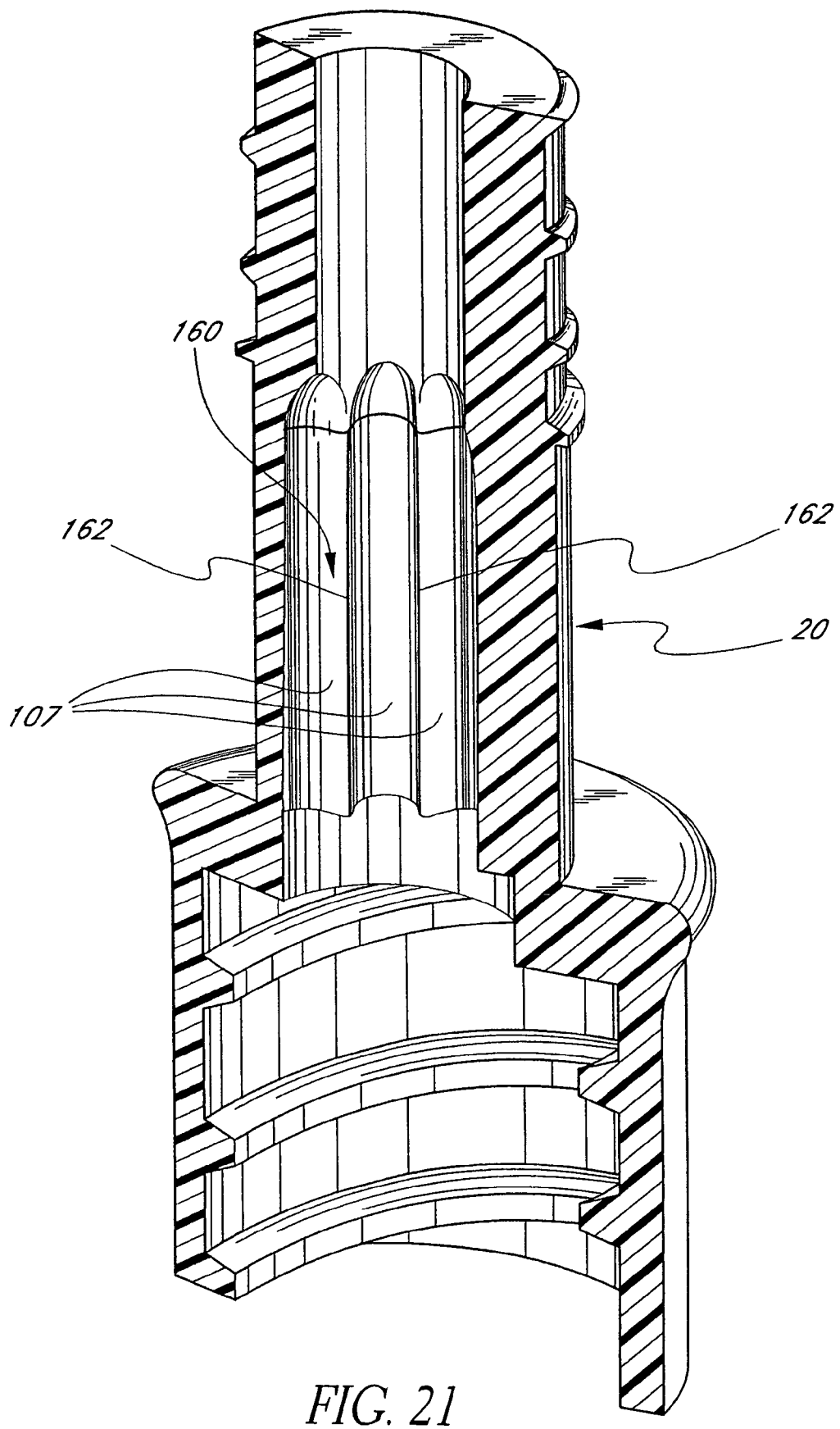
FIG. 21 is a perspective view, with sections broken away to show the wall structure of the cavity containing the seal shown in FIGS. 13 and 14.

As mentioned above, preferably seal 36d has a precut slit 11 in the cap 92 lying along the longitudinal axis of the valve 10. The seal cap 92 has a unique configuration that insures that the slit 11 closes and is sealed upon withdrawal of a syringe (not shown) and reformation of the seal 36d. It includes an enlarged, internal, pressure responsive member 200 which is integral with the cap 92. Between the proximal end of the side wall 150 and the member 200 is an annular space 102 which is filled with the fluid in the cavity 98. This fluid is under pressure, for example at the blood pressure of the patient to which the valve 10 is attached. Referring to FIG. 14, fluid, for example the patient's blood, flows through the holes 34 in the spike 26, filling the cavity 102. This fluid presses against the exterior of the member 200, closing the slit 11 when the seal is decompressed as shown in FIGS. 14 and 19. The pressure from this fluid creates a high pressure seal which prevents fluid from escaping valve 10 through the slit 11. There is a semi-cylindrical annular flange tear ring 104 on the end of the member 200 which advantageously extends the useful life of seal 36d.

Preferably, there is a tear ring 104 integral with the member 200 along the perimeter of the internal surface the member 200, and a slight saucer-like depression 204 in the external surface of the seal. The pressure responsive element in the decompressed state closes any orifice in the seal 36d to provide an essentially fluid-tight seal while in the decompressed state. The pressure responsive member 200 enables the valve to maintain a fluid-tight seal even at very high pressures sometimes experienced in medical applications, particularly when the valve 10 is connected to a patient's artery. The center of the member 200 and the annular space 102 are coaxial with the entryway 11a to the orifice 11. The pressurized fluid fills the annular space 102 to apply pressure that compresses the member 200 to tightly close the entryway to the orifice. In a preferred embodiment the distance from the entryway 11a to the proximal end of seal cap 92 is from 0.500 to 0.075 inches and more preferably approximately 0.100 inch.

Figure 22:
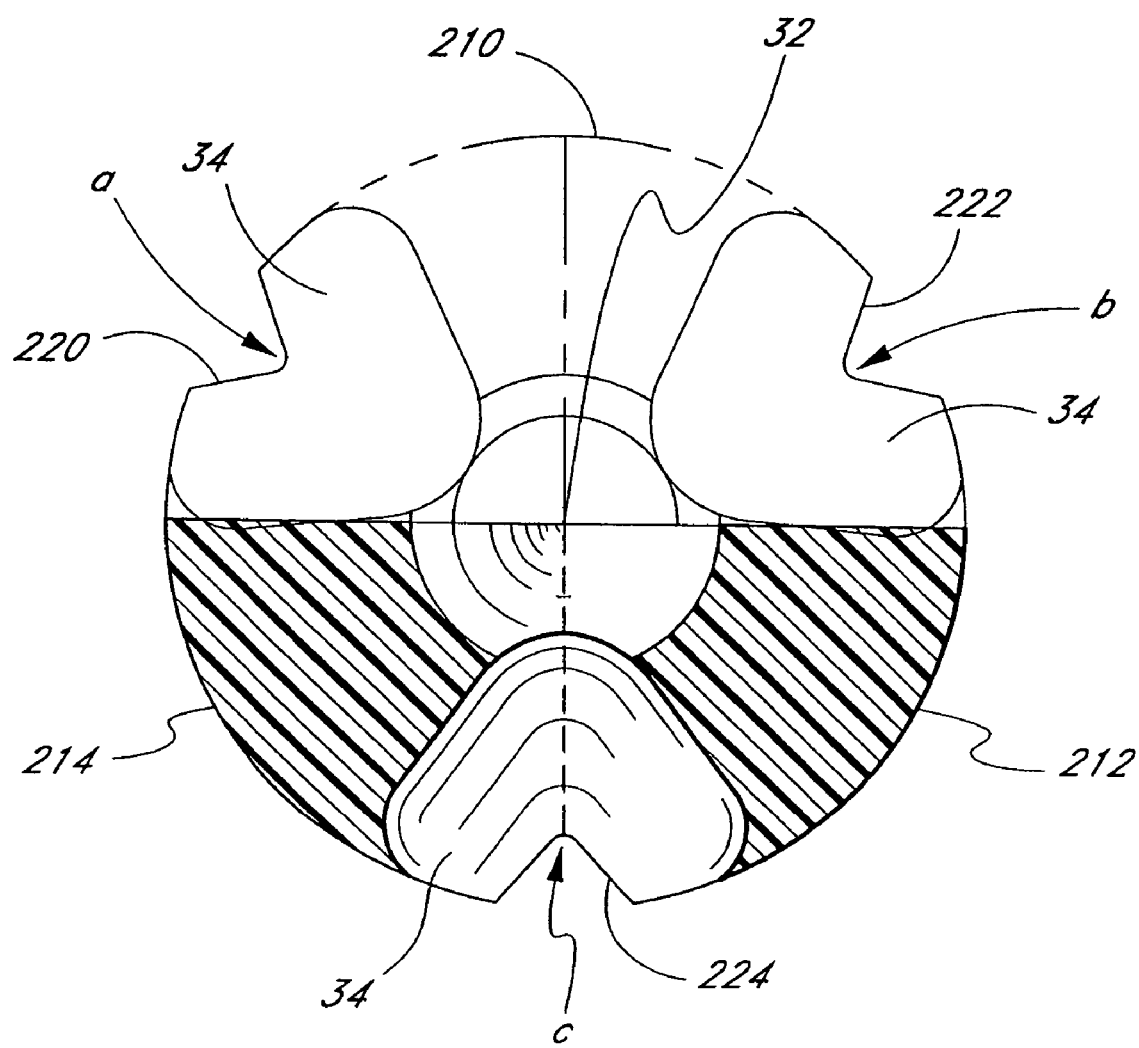
FIG. 22 is a greatly enlarged, cross-sectional view taken along line 22-22 of FIG. 14.

As best illustrated in FIG. 22, the tip 32 is designed to avoid tearing the seal. Tip 32 has three facets 210, 212, and 214 which are joined with each other along parting lines a, b, and c. This junction of the facets 210, 212, and 214 frequently is ragged and will tear the seal 36d. This is prevented by the parting lines a, b, and c, or junctions, being disposed within recesses 220, 222, and 224, respectively, to provide "buried parting lines."

Another alternative embodiment of the present invention using the seal 36d is shown in FIG. 8 and FIGS. 19 through 21. In this embodiment, the inner wall 160 of the upper end of the conduit 20 is provided with at least one, and preferably, a plurality of radial indentations 107. The indentations 107 are elongated disposed generally parallel to the longitudinal axis if the valve 10 in a symmetrical, star-like configuration. Each indentation has opposed lateral edges 162 which engage the seal 36d upon compression of the seal 36d. The indentations provide space into which the seal 36d expands upon compression.

Figure 8:
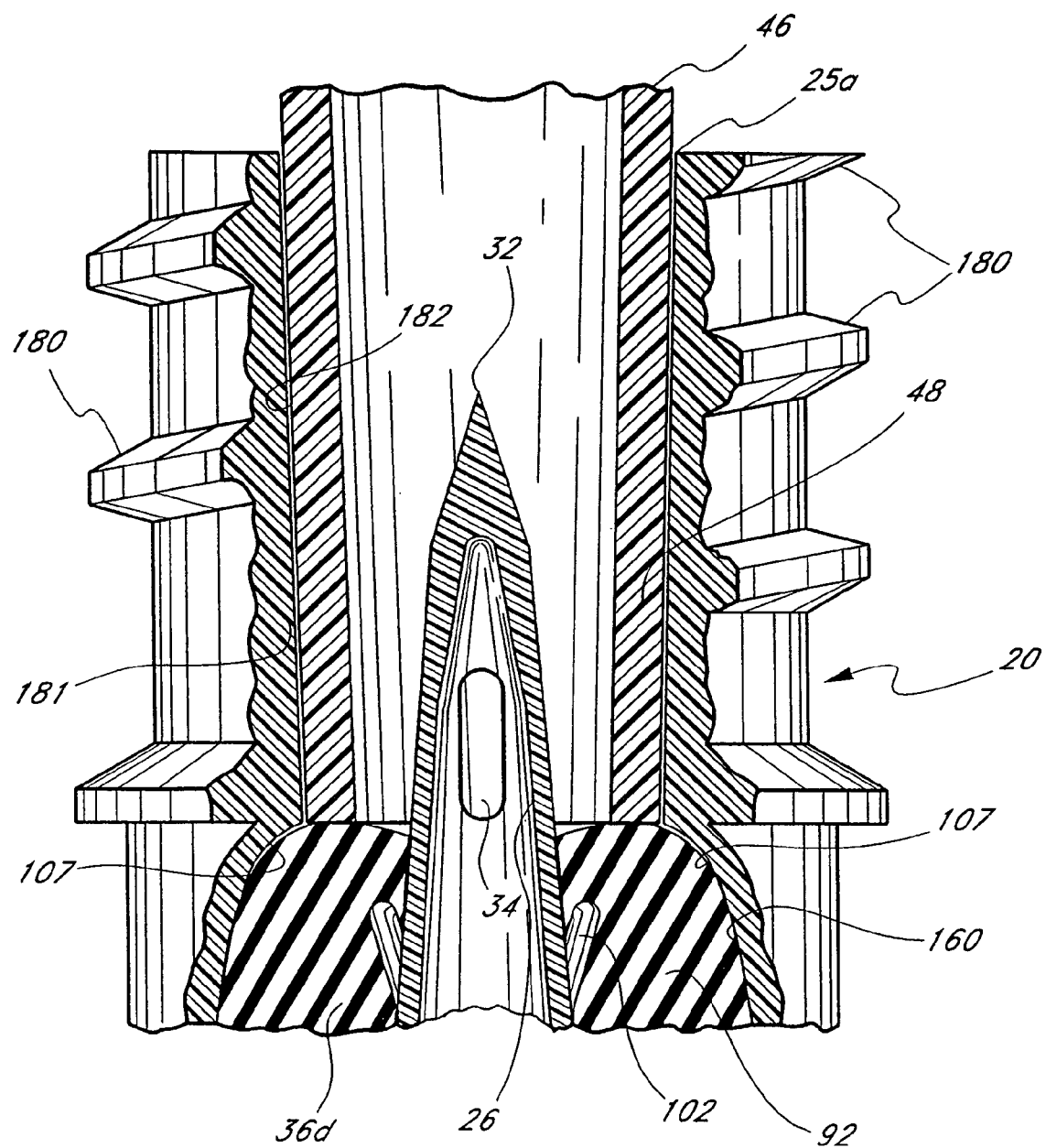
FIG. 8 is a schematic illustration of an ANSI delivery end of a medical implement compressing the seal of the valve of this invention.

As best shown in FIG. 8, the wall 181 of the proximal end of the conduit 20 is tapered inward at the same angle as the nose 48 of the syringe 46. In accordance with ANSI standards, the taper is 0.006 inch per linear inch. The wall 182 of the syringe nose 48 bears against the wall 181 as the nose slides into the opening 25a to push the seal 36d inward compressing it and forcing the tip 32 of the spike 36 to enter the slit 11. The seal 36d expands upon compression to fill essentially completely the upper portions of the indentations 107. Some sections of the seal 36d are wedged between the edges 162 and other sections fill the indentations 107. As the liquid flows through the nose 48 through holes 34, air in the nose 48 is forced out of the nose 48 and expelled from valve 10 between walls 181 and 182. Thus, essentially the entire prescribed dosage is delivered through valve 10 to the patient. Fluid flows through the through-holes 34, but does not leak between either the seal 36d and the wall 181 or between the abutting walls 181 and 182.

FIGS. 15, 16, 17, and 18 depict embodiments of seals, namely, seal 36e, seal 36f and seal 36g, which are substantially the same as the seals 36a (FIG. 10), seal 36b (FIG. 11), and seal 36c (FIG. 12), except the side wall 150 employing the circular tires 100 is used in place of the accordion wall portion 94. As shown in the Figures, the flexible seal element in the first position can include a first internal diameter in the main portion of the housing, a second internal diameter in the main portion distal the first internal diameter, and a third internal diameter in the main portion distal the second internal diameter. The second internal diameter in the main portion can be different than the first and third internal diameters in the main portion. Portions of the flexible element include a second internal diameter larger than the first and third internal diameters. In addition, portions of the flexible element include a second internal diameter larger than the first internal diameter and smaller than the third internal diameter.

Other components of the present invention interact with the various embodiments of the seal in a similar fashion to their interaction with seal 36 of FIG. 2. Prior to use of valve 10, it is preferable that the seal caps 40 or 92 be pierced centrally by a steel needle in the axial direction, precutting the seal to provide the slit 11 in order to allow for more rapid decompression and reformation of the seal upon piercing by the spike 26. The seals are advantageously formed from a material which can repeatedly reseal and prevent fluid from flowing around the seal material. The seal 36 should also be capable of being forced down and then spring back into position to reseal the valve. Material that is too soft will reseal effectively; however, will not be capable of springing back after opening of the valve. Material that is too hard will provide sufficient spring force; however, will not effectively seal. Thus, in a preferred embodiment, the seal is formed from a silicone having a hardness in the range from 30-70 Shore durometer units, and more preferably in the range 40-50 Shore durometer units. A cure silicone polymer in the preferred hardness range is available from Wacker Silicone Corp. of Adrian, Mich. In some embodiments of the invention, it is desirable to provide additional lubricity to the seal 36 to allow it to spring back and reseal more effectively. Dow Chemical Co. produces a silicone formulation with silicone oil built in to provide this additional lubricity.

In general, the closing of the valve 10 is provided not by the side wall of the seal 36 which immediately covers the through-holes 34, but by the seal cap 40, or seal cap 92 filling the proximal end of the cavity 98 and the opening 25a. Thus, the seal caps 40 and 92 are sufficiently thick to reseal the opening 25a effectively after valve closure. However, the seal caps 40 and 92 should also be sufficiently thin to allow them to readily return to the closed position. Preferably the thickness of the caps 40 and 92 ranges between 0.075 and 0.500 inch and more preferably may be approximately 0.100 inch.

The valve disclosed in this invention can be provided in a sterile and disposable form such that after its use in a given installation is exhausted, the device is discarded. However, as described above, in any given installation, the device can be reused multiple times. Since the device does not employ needles, there is little chance that the device will inadvertently cause skin puncture. Therefore, the extra precautions required for handling and disposing of needles is obviated. It will be apparent from the detailed description provided herein that the present invention can provide for the elimination of nearly all needles used in the medical environment. With the use of the valve of the present invention, the need for all needles except those that are directly input into a patient is, advantageously, eliminated.

Operation

The valve 10 is used to provide a closed, patient access system for transferring a predetermined amount of medication from a remote source to the patient. The valve 10 is connected by the distal end to the patient, for example, a vein or artery in fluid communication with the valve. Blood fills the valve, but the seal 36d, for example, prevents any blood from leaking from the valve. The delivery end or nose 48 of the medical implement is inserted into the valve as depicted in FIG. 8, pushing the nose 48 against the seal to compress the seal sufficiently to allow the tip 32 of the spike 24 to pierce the seal and enter said delivery end. The predetermined amount of medication in its entirety may now be transferred through the nose 48 into the valve 10 and into the patient. Since the nose 48 and seal 36d engage in a manner so that the tip 32 of the spike element 24, upon piercing the seal, meets the seal to avoid formation of any dead space at the interface between nose 48 and the seal surface 40b. Transfer directly through the valve 10 of essentially the entire predetermined amount of medication from the syringe 46 to the patient, so that essentially none of said predetermined amount is collected in any dead space in the valve, is accomplished with this invention. Upon withdrawing the nose 48 from the valve 10 the seal 36d returns to the decompressed state to close the valve and maintain while in said decompressed state a fluid tight seal even at high pressures and after repeated uses.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A medical connector for controlling the flow of fluid between a first medical implement and a second medical implement, the connector comprising:
   a valve comprising an opening adapted at its proximal end to receive a first medical implement and a wall structure defining an internal cavity, the cavity comprising a neck portion in fluid communication with the opening and a main portion distal the neck portion with a larger internal diameter than the neck portion;
   a flexible element positioned in the cavity, the flexible element movable between a first position in which the flexible element impedes fluid flow through the valve and a second position in which fluid flow is facilitated through the valve, the flexible element comprising a proximal end, a distal end, and a flexible wall with an inner surface and an outer surface, the flexible element in the first position being positioned essentially even with the wall structure at the opening of the valve to facilitate antiseptic swabbing of an outer surface of the proximal end of the flexible element and comprising a first internal diameter in the main portion, a second internal diameter in the main portion distal the first internal diameter, and a third internal diameter in the main portion distal the second internal diameter, the second internal diameter in the main portion being different than the first and third internal diameters in the main portion; and
   a rigid element configured to act as a fluid conduit through at least a portion of the valve.

2. A medical connector of claim 1, wherein the second internal diameter being larger than the first and third internal diameters.

3. A medical connector of claim 1, wherein the second internal diameter being larger than the first internal diameter and smaller than the third internal diameter.

4. The connector of claim 1, wherein the flexible wall of the flexible element defines an internal cavity and the proximal end of the flexible element further comprises an orifice extending from the outer surface of the proximal end to the internal cavity.

5. The connector of claim 4, wherein the shape of the proximal end of the flexible element is adapted to facilitate closure of the orifice when the flexible element is in the first position.

6. The connector of claim 1, wherein the proximal end of the flexible element has a generally circular cross-section when the flexible element is in the first position.

7. The connector of claim 4, wherein the proximal end of the flexible element has a generally circular cross-section when the flexible element is in the first position.

8. The connector of claim 1, wherein the cross-sectional widths of the neck portion and main portions of the valve are diameters spanning substantially circular cross-sections of the internal cavity.

9. The connector of claim 1, wherein at least a portion of the valve in a region of the internal cavity between the neck portion and the main portion has a tapered interior surface.

10. The connector of claim 1, wherein the connector provides substantially linear fluid flow from the first medical implement through the connector to the second medical implement.

11. The connector of claim 4, wherein the orifice is made before the flexible element is used to transfer fluid therethrough.

12. The connector of claim 1, wherein at least a portion of the flexible element is corrugated.

13. The connector of claim 1, wherein at least a portion of an outer surface of the flexible element is an imperforate bellows.

14. The connector of claim 1, wherein the flexible element moves between the first and second positions in an accordion-like fashion.

15. The connector of claim 1, wherein the flexible element comprises silicone rubber.

16. The connector of claim 1, wherein the proximal end of the flexible element at or near the proximal end of the valve in the first position fills essentially completely the opening in the proximal end of the valve in a horizontal cross-sectional dimension.

17. The connector of claim 1, wherein the rigid element facilitates a flow of fluid in a distal direction from the inside of the flexible element to a region outside of the flexible element.

18. The connector of claim 1, wherein the rigid element assists in supporting the flexible element within the internal cavity of the valve.

19. The connector of claim 1, wherein the rigid element assists in centering the flexible element within the internal cavity of the valve.

20. The connector of claim 1, wherein a proximal end of rigid element includes a pointed tip.

21. The connector of claim 20, wherein the pointed tip of the rigid element penetrates the flexible element when the flexible element is in the second position.

22. The connector of claim 1, wherein the rigid element is tapered.

23. A medical connector for controlling the flow of fluid between a first medical implement and a second medical implement, the connector comprising:
   a valve comprising an opening adapted at its proximal end to receive a first medical implement and a wall structure defining an internal cavity, the cavity comprising a neck portion in fluid communication with the opening and a main portion distal the neck portion with a larger internal diameter than the neck portion;
   a flexible element positioned in the cavity, the flexible element movable between a first position in which the flexible element impedes fluid flow through the valve and a second position in which fluid flow is facilitated through the valve, the flexible element comprising a proximal end, a distal end, and a flexible wall with an inner surface and an outer surface, the flexible element in the first position being positioned essentially even with the wall structure at the opening of the valve to facilitate antiseptic swabbing of an outer surface of the proximal end of the flexible element and comprising a first internal diameter in the main portion, a second internal diameter in the main portion distal the first internal diameter, and a third internal diameter in the main portion distal the second internal diameter, the second internal diameter in the main portion being different than the first and third internal diameters in the main portion; and a spike configured to act as a fluid conduit through at least a portion of the valve.

24. A medical connector of claim 23, wherein the second internal diameter being larger than the first and third internal diameters.

25. A medical connector of claim 23, wherein the second internal diameter being larger than the first internal diameter and smaller than the third internal diameter.

26. The connector of claim 23, wherein the flexible wall of the flexible element defines an internal cavity and the proximal end of the flexible element further comprises an orifice extending from the outer surface of the proximal end to the internal cavity.

27. The connector of claim 26, wherein the shape of the proximal end of the flexible element is adapted to facilitate closure of the orifice when the flexible element is in the first position.

28. The connector of claim 23, wherein the proximal end of the flexible element has a generally circular cross-section when the flexible element is in the first position.

29. The connector of claim 23, wherein at least a portion of the valve in a region of the internal cavity between the neck portion and the main portion has a tapered interior surface.

30. The connector of claim 26, wherein the orifice is made before the flexible element is used to transfer fluid therethrough.

31. The connector of claim 23, wherein at least a portion of the flexible element is corrugated.

32. The connector of claim 23, wherein at least a portion of an outer surface of the flexible element is an imperforate bellows.

33. The connector of claim 23, wherein the proximal end of the flexible element at or near the proximal end of the valve in the first position fills essentially completely the opening in the proximal end of the valve in a horizontal cross-sectional dimension.

* * * * *